(12) United States Patent
Rzhetsky et al.

(10) Patent No.: US 6,633,819 B2
(45) Date of Patent: Oct. 14, 2003

(54) GENE DISCOVERY THROUGH COMPARISONS OF NETWORKS OF STRUCTURAL AND FUNCTIONAL RELATIONSHIPS AMONG KNOWN GENES AND PROTEINS

(75) Inventors: Andrey Rzhetsky, New York, NY (US); Sergey Kalachikov, New York, NY (US)

(73) Assignee: The Trustees of Columbia University in the City of New York, New york, NY (US)

( * ) Notice: Subject to any disclaimer, the term of this patent is extended or adjusted under 35 U.S.C. 154(b) by 0 days.

(21) Appl. No.: 09/327,983

(22) Filed: Jun. 8, 1999

(65) Prior Publication Data

US 2002/0049542 A1 Apr. 25, 2002

Related U.S. Application Data

(60) Provisional application No. 60/129,469, filed on Apr. 15, 1999.

(51) Int. Cl.[7] ............................ G01N 31/00; G06F 15/00
(52) U.S. Cl. .............................. 702/27; 435/6; 708/131; 712/200
(58) Field of Search ................................ 435/6; 395/13, 395/11, 51; 708/131; 702/27; 712/200

(56) References Cited

PUBLICATIONS

Yuan et al., "Towards detection of orthologues in sequence databases," Bioinformatics, 1998, vol. 14, No. 3, pp. 285–289.*
Sonnhammer et al., "Pfam: A comprehensive database of protein domain families based on seed alignments," Protein Structure Function and Genetics, 1997, vol. 28, No. 3, pp. 405–420.*
Pearson, "Identifying distantly related protein sequences," CABIOS, 1997, vol. 13, No. 4, pp. 325–332.*
Grundy et al., "Meta–MEME: Motif–based hidden Markov models of protein families," CABIOS, 1997, vol. 13, No. 4, pp. 397–406.*
Ballinger CA et al., 1999, Mol. Cell. Biol. 19:4535–4545.
Barabasi and Albert, 1999, Science 286:509–512.
Enright AJ et al., 1999, Nature 402:86–90.
Marcotte EM et al., 1999, Science 285:751–753.
Ruecknagel KP et al., 1999, Dihydrolipoamide S–Succinyltransferase Precursor, Accession XUBYSD (gi|2144399).
Bailey et al., 1998, Genome Research 8:362–376.
Bono et al., 1998, Genome Res. 8:203–210.
Friedman C et al., 1998, Methods of Information Medicine 37: 334–44.
Goto S. et al., 1998, Nucleic Acid Research 14:591–599.
Grundy, 1998, J. Computational Biology 5: 479–491.
Hu et al., 1998, J. Biol. Chem. 273:33489–33494.
Sonnhammer ELL et al., 1998, Nucleic Acids Research 26 (1):320–322.
Wu SK et al., 1998, J. Biol. Chem. 273:26931–26938.
Altschul et al., 1997, Nucleic Acids Research 25:3389–3402.
Attwood TK et al., 1997, J. Chem. Inf. Comput. Sci 37:417–424.
Cserzo M et al., 1997, Protein Engineering 10: 673–676.
Goto et al., 1997, Pac. Symp. Biocomput. 2:175–186.
Grundy et al., 1997, Biochem Biophys. Res. Commun. 231(3):760–766.
Grundy et al., 1997, CABIOS 13:397–406.
Mushegian AR et al., 1997, Proc. Natl., Acad Sci USA 94:5831–5836.
Neuwald, 1997, Nucleic Acids Research 25:1665–1677.
Rogers MA et al., 1997, Differentiation 61:187–194.
Selkov E et al., 1997 Nucleic Acids Research 25:37–38.
Sharket et al., 1997, TIG 13:145–151.
Skvorak AB et al., 1997, Genomics 46:191–199.
Tatusov RI et al., 1997, Science 278;631–637.
Boskovic J et al., 1996, Transcription Factor GRF10, Accession A25872 (gi|82888).
Felsenstein J et al., 1996, Methods in Enzymology 266:418–427.
Gustsfsson C et al., 1996, Nucleic Acids Research 24:3756–3762.
Jain NL et al., 1996, Proc. AMIA Annu Fall Symp. pp. 542–546.
James CM et al., 1996, Cell Division Control Protein CDC43, Accession RGBY43 (gi|2144611).
Koonin EV et al., 1996, Methods in Enzymology 266:295–323.
Mathews S et al., 1996, Mol. Biol. Evol. 13:1141–1150.
Miklos GLG et al., 1996, Cell 86:521–529.
Selkov et al., 1996, Nucleic Acids Research 24:26–28.
Wu CH et al., 1996, Comput. Appl. Biosci 12:109–118.
Bailey et al., 1996, Proc Int Conf Intell Syst Mol Biol. 3: 21–29.
Green PJ, 1995, Biometrika 82:711–732.
Hripcsak G. et al., 1995, Ann. Intern Med. 122:681–688.
Neuwald AF et al., 1995, Protein Sci. 4:1618–1632.
Purnelle B et al., 1995, Pre–mRNA Splicing Factor PRP21, Accession S 23553 (gi|280467).

(List continued on next page.)

Primary Examiner—Kenneth R. Horlick
Assistant Examiner—Young Kim
(74) Attorney, Agent, or Firm—Baker Botts L.L.P.

(57) ABSTRACT

The present invention relates to methods for identifying novel genes comprising: (i) generating one or more specialized databases containing information on gene/protein structure, function and/or regulatory interactions; and (ii) searching the specialized databases for homology or for a particular motif and thereby identifying a putative novel gene of interest. The invention may further comprise performing simulation and hypothesis testing to identify or confirm that the putative gene is a novel gene of interest.

2 Claims, 26 Drawing Sheets

Microfiche Appendix Included
(3 Microfiche, 131 Pages)

OTHER PUBLICATIONS

Yang Z et al., 1995, *Syst. Biol.* 44:384–399.

Churcher C, 1994, Dihydrolipoamide Dehydrogenase Precursor, Accession A 30151 (gi|82983).

Contreras R et al., 1994, Hypothetical Protein YBL067C, Accession S45803 (gi|626480).

Entian KD et al., 1994, Omnipotent Suppressor Protein SUP45, Accession S46014 (gi|626763).

Gaillon L et al., 1994, Transcription Factor BASI, Accession A 40083 (gi|101447).

Hamlyn N et al., 1994, Oxoglutarate Dehydrogenase Precursor, Accession DEBY (gi|1070439).

Kazic 1994, In: *Molecular Modeling:From Virtual Tools to Real problems*, Kumosinski, T. and Liebman, M.N. (Eds.), American Chemical Society, Washington, D.C. pp. 486–494.

Kazic, 1994, In: *New Data Challenges in Our Information Age* Glaesar, P.S. and Millward, M.T.L (Eds.). Proceedings of the Thirteenth International CODATA Secretariat, Paris pp. C133–C140.

Krogh et al., 1994, *J. Mol. Biol.* 235:1501–1531.

Murphy L et al., 1994, Suppressor 2 Protein, Accession EFBY52 (gi|72877).

Rieger M, 1994, Protein Farnesyltransferase Chain RAM2, Accession P29703 (gi|266880).

Tatusov RL et al., 1994, Proc. Natl Acad. Sci. USA 91:12091–12095.

Orengo et al., 1993, *J Mol Biol* 233(3):488–497.

Ullrich O et al., 1993, *J. Biol. Chem.* 268:18143–18150.

Peitgen HO, Juregens H, Saupe D, 1992, *Chaos and Fractals: New Frontiers of Science*, Springer Verlag, New York.

Altschul et al., 1990, *J. Mol. Biol.* 215:403–410.

Goldman N 1990, *Syst. Zoo.* 39:345–361.

Karlin S et al., 1990, *Proc. Natl. Acad. Sci. USA* 87:2264–2268.

Pamilo P et al., 1988, *Mol. Biol. Evol* 5:568–583.

Saitou N, 1987, *Mol. Biol. Evol.* 4:406–425.

Fitch WM, 1974, *J. Mol. Evol.* 3:263–278.

Felsenstein J, 1978, *Syst. Zool.*, 27:401–410.

Fitch WM, 1970, *Syst. Zool.*, 19:99–113.

Hastings, 1970, *Biometrika* 57:97–109.

\* cited by examiner bcl-xL / bcl / bcl-xS / ced-9 / Bax / Blk / Bak / p21 / NGFI-B / N10 /Nak1 / Nur77 / Nurr 1 / Nor-1 / Noi-1 / RXR/ galectin-1 / N-glycan / CNTF / lck / fyn / ZAP-70 / raf / ras / MAP / protein kinase C / PKC / phosphatase calcineurin / NF-AT / AP1 / 14-3-3 / Raf-1 / Bcl-2 / interieukin / IL-1 / IL-3 / cytokine / IGF-1 / CD95 / Apo-1 / RIP / FAF1 / FADD / FAP-1 / TNFR / TRAF / TRAP1 / TRAP2 / TRADD / HIAP1 / HIAP2 / CD40 / CD30 / XIAP / CD2 / CD3 / TCR / Bcl-w / Mci-1 / NR-13 / BHRF1 / HMW5-HL / E1B19K / Nbk / Mch2 / CPP32 / ICE / FLICE / Nedd-2 / TX / Mch3 / Mch4 / ICB-1s / nor-1 / DNAseI / caspase / MACH1 / Mch5 / apopain / Yama / ICH / CMH / ced-3 / ced-4 / ced-9 / p53 / MKK3 / MKK1 / MKK2 / MKK4 / BAG-1 / Src / FAST/ p38 / p42 / ERK1 / p44 / ERK2 / SAPK / JNK / MEK / C-JUN / MEF2D / ATF2 / calcineurin / ELK-1 / protein phosphatase 2A / raf-1 / IL-1 beta / TNF / PTK / Apaf / p35 / ETS / C-Myc / IL-2 / IL-2 receptor / NF-kappa B / TNFR-1 / TRAIL / APO-2L / DR4 / death receptor / DR3 / DR2 / DR5 / DR1 / bod / BMPR / BMP-x / TGF / grim / bid / FAN / perforin / Fas-L / Fas / DcR1 / decoy receptor / wxi-1 / NGF receptor / growth factor / RAR

FIG.3

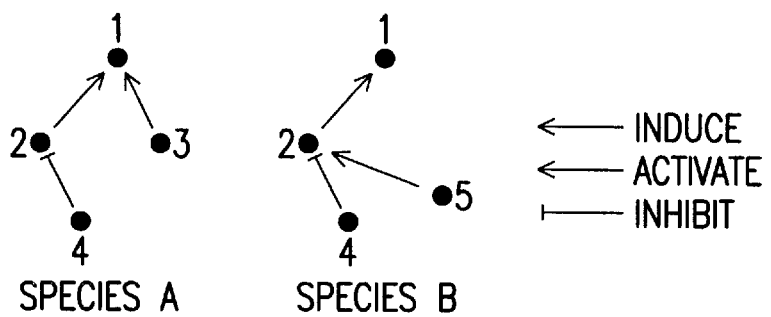
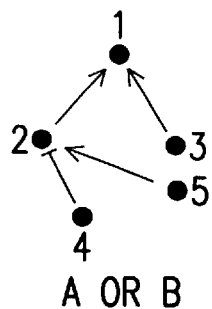
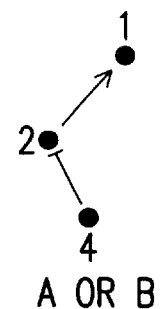
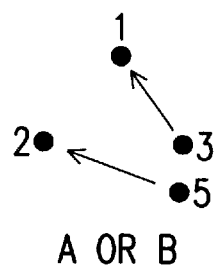
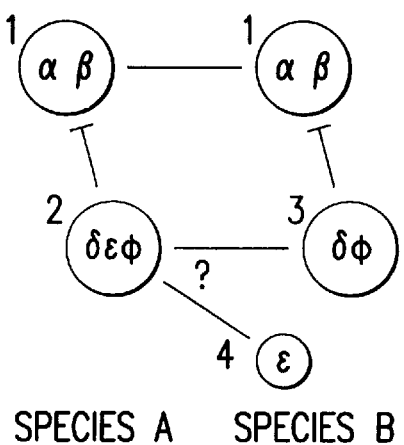

LEGEND FOR FIGS. 12A, 12B, AND 12C:

- ☆ POZ/BTB DOMAIN
- ○ KELCH REPEAT
- ⊙ RING FINGER DOMAIN
- ▭ FIBRONECTIN III DOMAIN
- ⬡ CYCLIN REPEAT
- □ EGF-LIKE DOMAIN
- ⬭ CUB DOMAIN
- △ LAMININ EGF-LIKE DOMAIN
- ⇡ TRANSMEMBRANE HELIX
- ○ BP-BIPARTITE NUCLEAR LOCALIZATION SIGNAL
- ▭ TRANSFERASE DOMAIN
- ⬡ NEW A-DOMAIN
- □ NEW POZ-LINKER DOMAIN
- ▭ NEW B-DOMAIN
- ○ NEW SPOP DOMAIN
- ▯ NEW (?) TN (TUMOR NECROSIS) DOMAIN
- ○ FOS/JUN DNA-BINDING DOMAIN
- ⌂ gi|1707204-DOMAIN
- ⬥ NEW HAT DOMAIN (HEMAGGLUTININ, ALPHA TOXIN, TUMOR NECROSIS-FACTOR-ALPHA-INDUCED PROTEIN)
- ⊗ DEATH DOMAIN
- ◇ KINASE DOMAIN
- ⇧ HEAT REPEAT
- ⊛ Zn-FINGER C$_2$H$_2$
- ▭ PROLINE-RICH REGION
- ▱ PKC-C1 DOMAIN, GAG/PE-BINDING
- ▱ PKC-C2 DOMAIN
- ○ PROTEIN KINASE DOMAIN

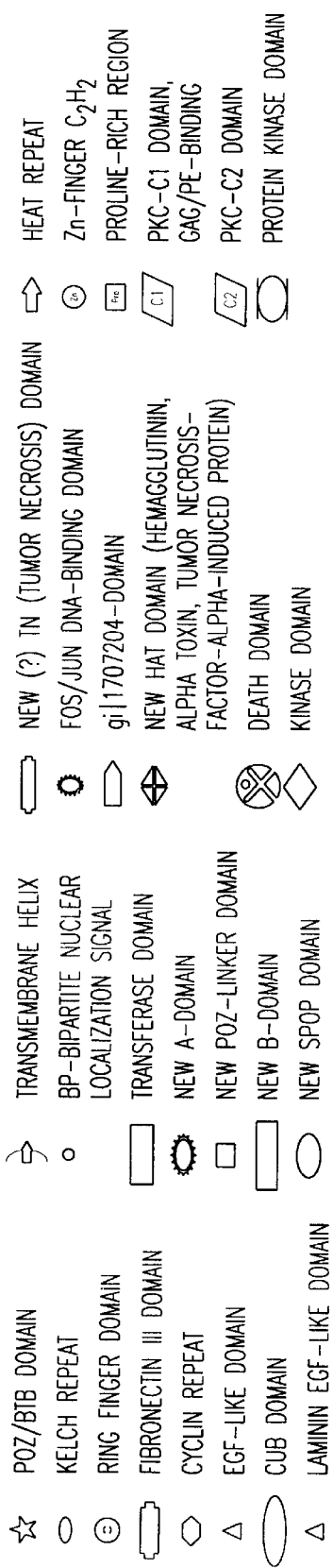

gi|2274880 gi|2274882, gi|2274884,
gi|2276170 gi|1397285

gi|2497611 gi|2414340 gi|1216123, gi|732215, gi|2226406, gi|1353147, gi|1070084, gi|1711486

>gi|2210766|gb|AA481214|AA481214 aa34e02.r1 NCI_CGAP_GCB1 Homo sapiens cDNA clone IMAGE:815162 5' similar to WP:W07A12.4 CE03795 :, mRNA sequence [Homo sapiens]
CATGGCTTCCTGGACACCAACCCTGCCATCCGGGAGCAGACGGTCAAGTTCATGTGCTCCTGGCCCCAA
AGCTGAACGAGGCCAACCTCAATGTGGAGCTGATGAAGCACTTTGCACGGCTACAGGCCAAGATGAACA
GGGCCCCATCCGCAACACCAGTCTGCCTGGGCAAAATGGCTTCCTACCTCAGTGCTAGCACCAGA
CACAGGGTCCTTACCTCTGCCTTCAGCCGAGCCACTAGGACCCGTTTGCACCGTCCCGGGTTGCGGGTG
TCCTGGGCTTTGCTGCCACCCACACGTCTGAGAAATCCGTGCGAGACCAGGCCTTCAAGGCA
CTGCGGGTCTCACTGTAGATCCTGAGAAATCCGTGCCGAGACCAGGCCTTCAAGGCA      ID8

>gi|1349211|gb|W51957|W51957 zc45f01.r1 Soares_senescent_fibroblasts_NbHSF Homo sapiens cDNA clone IMAGE:325273 5', mRNA sequence [Homo sapiens]
CCTTCGAGTTCGGCAATGCTGGGGCCGTTGTCCTCACGCCCCTCTTCAAGGTGGCAAGTTCCTGAGCGC
TGAGGAGTATCAGCAGAAGATCATCCCTGTGGTGGTCAGCAGTTCATCCAGTGGTGAACAGTTCTCATCCACTGACCGGGCCATGCGC
ATCCGNCTCCTGCAGCAGATGGAGCAGTTCATCCAGTACCTTGACGAGCCAACAGTCAACACCAGATCT
TCCCCACGTCGTACATGGCTTCCTGGACACCAACCCTGCCATCCGGGAGCAGACGGTCAAGTCCATGCT
GCTCCTGGCCCCAAAGCTGAACGAGGCCAACCTCAATGTGGAGCTGATGAAGCACTTTGCACGGCTACAG
GCCAAGGATGAACAGGGCCCCATCCGCAACACCACAGTCTGCCTGGGCAAAATGGCTTCCTACCTCA
GTGCTAGCACCAGACACACAGGGGTCCTTACCTCTG      ID9

FIG.13A

BASE COUNT 405 a   545 c   493 g   278 t   6 others
ORIGIN
   1 cagccgaagc amgcaaaaat tcttccagga gctgagcaag agcctggacg cattccctga
  61 ggayttctgt cggcacaagg tgctgcccca gctgctgacc gccttcgagt tcggcaatgc
 121 tggggccgtt gtcctcacgc ccctcttcaa ggtgggcaag ttcctgagcg ctgaggagta
 181 tcagcagaag atcatccctg tggtggtcaa gatgttctca tccactgacc gggccatgcg
 241 catccgcctc ctgcagcaga tggagcagtt catccagtac cttgacgagc aacagtcaa
 301 cacccagatc ttcccccacg tcgtacatgg cttcctggac accaaccctg ccatccggga
 361 gcagacggtc aagtccatgc tgctcctggc cccaaagctg aacgaggcca acctcaatgt
 421 ggagctgatg aagcactttg cacggctaca ggccaaggat gaacagggcc ccatccgctg
 481 caacaccaca gtctgcctgg gcaaaatcgg ctcctacctc agtgctagca ccagacacag
 541 ggtccttacc tctgccttca gccgagccac tagggacccg tttgcaccgt cccggggttgc
 601 gggtgtcctg ggctttgctg ccacccacaa cctctactca atgaacgact gtgcccagaa
 661 gatcctgcct gtgctctgcg gtctcactgt agatcctgag aaatccgtgc gagaccaggc
 721 cttcaaggcm wttcggagct tcctgtccaa attggagtct gtgtcggagg acccgaccca
 781 gctggaggaa gtggagaagg atgtccatgc agcctccagc cctggcatgg gaggagccgc
 841 agctagctgg gcaggctggg cgtgaccggg gtctcctcac tcacctccaa gctgatccgt
 901 tcgcacccaa ccactgcccc aacagaaacc aacattcccc aaagacccac gcctgaagga
 961 gttcctgccc cagcccccac ccctgttcct gccaccccta caacctcagg ccactgggag
1021 acgcaggagg aggacaagga cacagcagag gacagcagca ctgctgacag atgggacgac
1081 gaagactggg gcagcctgga gcaggaggcc gagtctgtgc tggcccagca ggacgactgg
1141 agcaccgggg gccaagtgag ccgtgctagt caggtcagca actccgacca caaatcctcc
1201 aaatccccag agtccgactg gagcagctgg gaarctgagg gctcctggga acagggctgg
1261 caggagccaa gctcccagga gccacctyct gacggtacac ggctggccag cgagtataac
1321 tggggtggcc cagagtccag cgacaagggc gacccctccg ctaccctgtc tgcacgtccc
1381 agcacccagc cgaggccaga ctcttggggt gaggacaact gggagggcct cgagactgac
1441 agtcgacagg tcaaggctga gctggcccgg aagaagcgcg aggagcggcg gcgggagatg
1501 gaggccaaac gcgccgagag gaaggtgcca agggccccat gaagctggga gcccggaagc
1561 tggactgaac cgtggcggtg gcccttcccg gctgcggaga gcccgcccca cagatgtatt
1621 tattgtacaa accatgtgag cccggccgcc cagccaggcc atctcacgtg tacataatca
1681 gagccacaat aaattctatt tcacaaaaaa aaaaaaaaaa aaaaaaa
//

>sp|P15533|RPT1_MOUSE DOWN REGULATORY PROTEIN OF INTERLEUKIN 2 RECEPTOR
(J03776) rpt-1r [Mus musculus] Length = 353

Score = 92.0 bits (237), Expect = 6e-20

```
Query  194  VMELLEEDLTCPICCSLFDDPRVLPCSHNFCKKCLEGILEGSVRNSMWRPAPFKCPTCRK  373
            V+E+++E++TCPIC  L +P   C+H+FC+ C+    E S RN+       CP CR
Sbjct    5  VLEMIKEEVTCPICLELLKEPVSADCNHSFCRACITLNYE-SNRNT---DGKGNCPVCRV   60

Query  374  ETSATGINSLQVNYSLKGIVEKYNKIKISP----KMPVCKGHMGQPLNIFCLTDMQLICG  541
              +L+ N +  IVE+    K P    K+ +C  H G+ L +FC  DM +IC
Sbjct   61  PYP---FGNLRPNLHVANIVERLKGFKSIPEEEQKVNICAQH-GEKLRLFCRKDMMVICW  116

Query  542  ICATRGEHTKHVFCSIEDAYAQERDAFESLFQSF-------ETWRRGDALSRLDTMETSK  700
            +C   EH H   IE+  + ++  +            + W+    L R+D
Sbjct  117  LCERSQEHRGHQTALIEEVDQEYKEKLQGALWKLMKKAKICDEWQDDLQLQRVDW-----  171

Query  701  RKSLQLMTKDSDKVKEFFEKLQHTLDQKKNEILSDFETMKLAVMQAYDPEINKL  862
              +Q+   + + V+   F+ L+   LD K+NE L    K  VM+  +   N+L
Sbjct  172  ENQIQI---NVENVQRQFKGLRDLLDSKENEELQKLKKEKKEVMEKLEESENEL  222
```

Homology covers ring finger, B-box and the beginning of coiled coil domain
in the CLL ring finger protein

FIG.14

ACTIVATED CD4⁺ T-CELLS
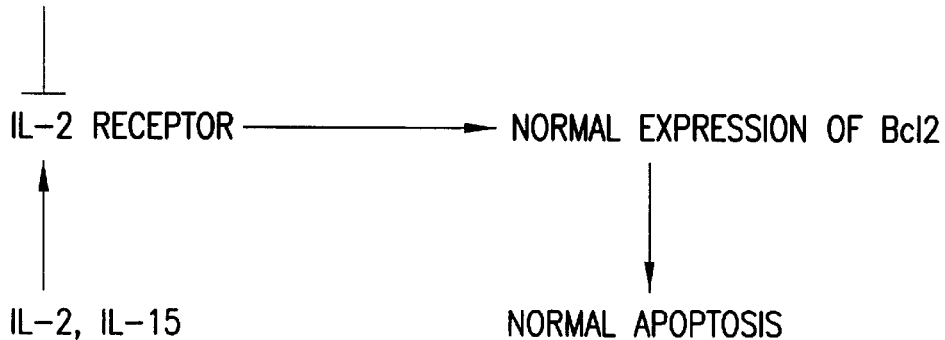
WHEN rpt1 IS KNOCKED OUT:
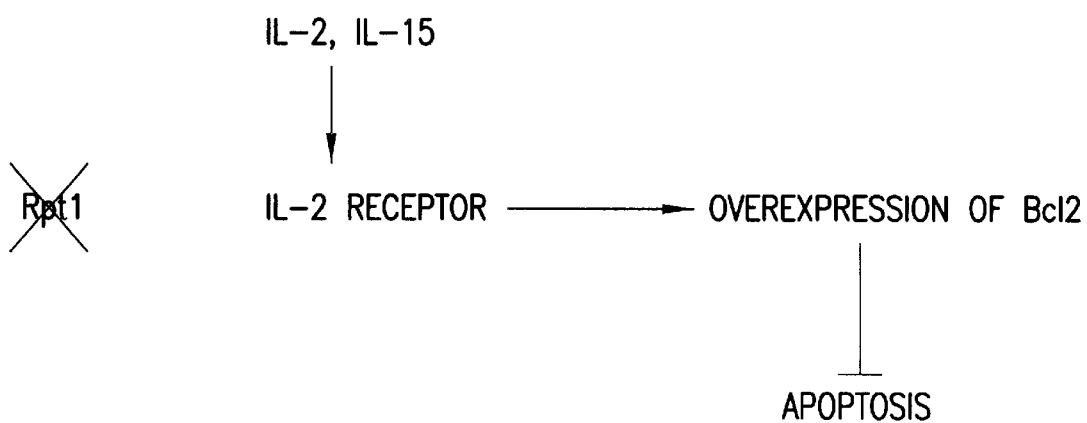
FIG.15

TBLASTN 2.0.8 [Jan-05-1999]

Reference:
Altschul, Stephen F., Thomas L. Madden, Alejandro A. Schaffer,
Jinghui Zhang, Zheng Zhang, Webb Miller, and David L. Lipman (1997),
"Gapped BLAST and PSI-BLAST: a new generation of protein database search
programs", Nucleic Acids Res. 25.3389-3402.

Query= gi |2137498|Mad3m
       (205 letters)

gb|AA278224|AA2278224 zs77e05.r1 NCI_CGAP_GCB1 Homo sapiens cDNA clone IMAGE:703520 5'
           similar to TR:G1184157 G1184157 MAX-INTERACTING
           TRANSCRIPTIONAL REPRESSOR. ;
           Length = 430

Score =  209 bits (526), Expect = 1e-53
 Identities = 104/124 (83%), Positives = 116/124 (92%), Gaps = 1/124 (0%)
 Frame = +2

Query: 1    MEPVASNIQVLLQAAEFLERREREAEHGYASLCPHHSPGTVCRRRKPPLQAPGALNSGRS  60    ID14
            MEP+ASNIQVLLQAAEFLERREREAEHGYASLCPH SPG + RR+K P QAPGA +SGRS        ID15
Sbjct: 56   MEPLASNIQVLLQAAEFLERREREAEHGYASLCPHRSPGPIHRRKKRPPQAPGAQDSGRS  235   ID16

Query: 61   VHNELEKRRRAQLKRCLEQLRQQMPLGVDCTRYTTLSLL-RARVHIQKLEEQEQQARRLK  119
            VHNELEKRRRAQLKRCLE+L+QQMPLG DC RYTTLSLL RAR+HIQKLE+QEQ+AR+LK
Sbjct: 236  VHNELEKRRRAQLKRCLERLKQQMPLGGDCARYTTLSLLRRARMHIQKLEDQEQRARQLK  415

Query: 120  EKLRS 124
            E+LR+
Sbjct: 416  ERLRT 430 dbj|C02407|C02407 HUMGS0012279, Human Gene Signature, 3'-directed cDNA sequence.
           Length = 348

Score = 97.5 bits (239), Expect = 6e-20
 Identities = 51/63 (80%), Positives = 56/63 (87%)
 Frame = +3

Query: 125  KQQSLQQQLEQLQGLPGARERERLRADSLDSSGLSSERSDSDQEDLEVDVENLVFGTETE  184   ID17
            KQQSLQ+    QL+GL GA ERERLRADSLDSSGLSSERSDSDQE+LEVDVE+LVFG E E       ID18
Sbjct: 45   KQQSLQRXWMQLRGLAGAAERERLRADSLDSSGLSSERSDSDQEELEVDVESLVFGGEAE  224   ID19

Query: 185  LLQ 187
            LL+
Sbjct: 225  LLR 233

FIG.16A

BASE COUNT   130 a     234 c     258 g     106 t       5 others
ORIGIN
     1  cagccgcttg ctccggccgg caccctaggc cgcagtccgc caggctgtcg ccgacatgga
    61  acccttggcc agcaacatcc aggtcctgct gcaggcggcc gagttcctgg agcgccgtga
   121  gagagaggcc gagcatggtt atgcgtccct gtgcccgcat cgcagtccag gccccatcca
   181  caggaggaag aagcgacccc cccaggctcc tggcgcgcag gacagcgggc ggtcagtgca
   241  caatgaactg gagaagcgca ggagggccca gttgaagcgg tgcctggagc ggctgaagca
   301  gcagatgccc ctgggcggcg actgtgcccg gtacaccacg ctgagcctgc tgcgccgtgc
   361  caggatgcac atccagaagc tggaggatca ggagcagcgg gcccgacagc tcaaggagag
   421  gctgcgcaca aagcagcaga gcctgcagcg gcantggatg cagctccggg ggctggcagg
   481  ngcggccgag cgggagcgnc tgcgggcgga cagtctggac tcctcaggcc tctcctctga
   541  gcgctcagac tcagaccaag aggagctgga ggtggatgtg gagagcctgg tgtttggggg
   601  tgaggccgag ctgctgcggg gcttcgtcgc cggccaggag cacagctact cgcacgtcgg
   661  cggcgcctgg ctatgatgtt cctcacccan ggcgggcctc tgccctctta ctcgttgccc
   721  aagcccactt tnc

```
>Mad3b(Putative)
MEPLASNIQVLLQAAEFLERREREAEHGYASLCPHRSPGPIHRKKRPPQAPGAQDSGRSVHNELEKRRRAQLK
RCLERLKQQMPLGGDCARYTTLSLLRRARMHIQKLEDQEQRARQLKERLRTKQQSLQRXWMQLRGLAGAAERER
LRADSLDSSGLSSERSDSDQEELEVDVESLVFGGEAELLRGFVAGQEHSYSHVGGAWL
```

FIG. 16C

| | | |
|---|---|---|
| gi\|2506888\|MADe | MATAVGHNIQLLLEAADYLERREREAEHGYASMLPYS-KDADAFKRRNKPKNST--SSRSTHNEMEKNRRAHLRLCLEKILKGLVPLGPESSRHTTLSLL | ID21 |
| gi\|729978\|MADh | MAAAYRMNIQMLLEAADYLERREREAEHGYASMLPYNNKDRDALKRRNKSKKNNS--SSRSTHNEMEKNRRAHLRLCLEKLLGLVPLGPESSRHTTLSLL | 22 |
| gi\|2792362\|Mad4h | ---MELNSLLILLEAAEYLERRDREAEHGYASVLPFDGDFAREKTKAAGLVRKAP--NNRSSHNELEKHRRAKLRLYLEQLKQLVPLGPDSTRHTTLSLL | 23 |
| gi\|217199\|Mad4m | ---MELNSLLLLLEAAEYLERRDREAEHGYASMLPFDGDFARKKTKTAGLVRKGP--NNRSSHNELEKHRRAKLRLYLEQLKQLGPLGPDSTRHTTLSLL | 24 |
| gi\|2137199\|Mad3m | -MEPVASNIQVLLQAAEFLERREREAEHGYASLCPHHSPGTVCRRRKPPLQAPGALNSGRSVHNELEKRRRAQLKRCLEQLRQQMPLGVDCTRYTTLSLL | 25 |
| Mad3h Putative | -MEPLASNIQVLLQAAEFLFRREREAEHGYASLCPHRSPGPIHRKKRPPQAPGAQDSGRSVHNELEKRRRAQLKRCLERLKQQMPLGGDCARYTTLSLL | 26 |
| | | |
| gi\|2506888\|MADe | TKAKLHIKKLEDCDRKAVHQIDQLQREQRHLKRRLEKLGAERTR------------MDSVG-SVVSSERSDSDREELDVDVDVDVEGTDYLPGDLGWSSS- |
| gi\|729978\|MADh | TKAKLHIKKLEDCDRKAVHQIDQLQREQRHLKRRLEKLGIERIR------------MDSIG-STVSSERSDSDRE-------EIDVDVESTDYLTGDLDWSSSS |
| gi\|2792362\|Mad4h | KRAKVHIKKLEEQQRRALSIKEQLQREHRFLKRRLEQLSVQSVER-----VRTDSTG-SAVSTD--DSEQE-------------VDIEGMEFGPGELDSVGS- |
| gi\|2137499\|Mad4m | K-AKMHIKKLEEQQRRALSIKEQLQREHRFLKRRLEQLSVQSVR------VRTDSTG-SAVSTD--DSEQE-------------VDIEGMEFGPGELDSAGS- |
| gi\|2137498\|Mad3m | R-ARVHIQKLEEQEQQARRLKEKLRSKQQSLQQQLEQLQGLPGARERPRLRADSLDSSGLSSERSDSDQE----------DLSVDVENLVFG-TETELLQSF |
| Mad3h Putative | RRARMHIQKLEDQEQRARQLKERLRTKQQSLQRXWMQLRGLAGAAERERLRADSLDSSGLSSERSDSDQE----------ELEVDVESLVFG-GEAELLRGF |
| | | |
| gi\|2506888\|MADe | VSDSDERGSMQSLG-SDEGYSSATVKRAKLQQGHKAGLGL |
| gi\|729978\|MADh | VSDSDERGSMQSLG-SDEGYSSTSIKRIKLQQGHKACLGL |
| gi\|2792362\|Mad4h | SSDADDHYSLQSGTGGDSGFGPHCRRLGRPALS------- |
| gi\|2137499\|Mad4m | SSDADDHYSLQSSGCSDSSYGHPCRRPGCPGLS------- |
| gi\|2137498\|Mad3m | SAGREHSYSHSTCAWL------------------------ |
| Mad3h Putative | VAGQEHSYSHVGGAWL------------------------ |

FIG. 16D

GENE DISCOVERY THROUGH COMPARISONS OF NETWORKS OF STRUCTURAL AND FUNCTIONAL RELATIONSHIPS AMONG KNOWN GENES AND PROTEINS

This application claims the benefit of Provisional Application No. 60/129,469, filed Apr. 15, 1999.

SPECIFICATION

The present specification contains a 3 page computer program listing which appears as a microfiche (3 frames) and 131 frames.

1. INTRODUCTION

The present invention relates to methods for identifying novel genes comprising: (i) generating one or more specialized databases containing information on gene/protein structure, function and/or regulatory interactions; and (ii) searching the specialized databases for homology or for a particular motif and thereby identifying a putative novel gene of interest. The invention may further comprise performing simulation and hypothesis testing to identify or confirm that the putative gene is a novel gene of interest.

Specifically, the present invention provides for the generation of specialized databases containing information on gene/protein structure, function and regulatory interactions based on the retrieval of such information from research articles and databases, and computer representation of such information in a manner that allows efficient access to the extracted information. The invention further provides for the use of the specialized databases for identifying novel genes based on detection of sequence similarities and domain/motif matches between genes/proteins, computation and interpretation of phylogenetic trees for multigene families, and analysis of homologous regulatory networks. The methods of the invention are based on the observation that functionally similar regulatory systems are generated during evolution by genetic duplication of ancestral genes. Thus, a comparison of homologous/similar networks within the same organism and between different species will allow the identification of genes absent in one of the systems under comparison. In this way genes that contribute to the phenotype of a specific disease associated with a particular biological system under analysis may be identified.

2. BACKGROUND OF THE INVENTION

A variety of different methods are currently utilized for the identification and characterization of novel genes. Perhaps the most widely used method for generating large quantities of sequence information is via high throughput nucleotide sequencing of random DNA fragments. A disadvantage associated with this gene discovery technique is that in most instances when genes are identified their function is unknown.

For identification of specific disease genes, positional cloning is currently the most efficiently used method. The positional cloning approach combines methods of formal genetics, physical mapping and mutation analysis and usually starts with a precise description of the disease phenotype and a tracing of the disease through families of affected individuals. Genetic linkage data obtained from the analysis of affected families frequently allows the determination of an approximate genomic localization of the candidate disease gene with a precision of several millions of nucleotides. Once localized, the genetically defined chromosomal region is then recovered from genomic libraries as a contiguous set of genomic fragments. Genes residing in the disease-related region are determined by analysis of transcripts that are transcribed from the genomic fragment. From this analysis an initial set of candidate genes for a particular disease are identified based on the presence of the gene product in the biological system affected by disease and a correlation between its expression pattern and the pattern of disease progression.

Important information for selection of candidate genes also comes from analysis of their homology with genes known to be part of the same or related biological system. Finally, the ultimate proof of association between a gene and a genetic disorder comes from mutational analysis of a gene in patients affected by the disorder and from demonstration of a statistical correlation between occurrence of mutation and the disease phenotype.

Although positional cloning is a powerful method for gene discovery, the experimental method is extremely tedious and expensive. Moreover, disease genes implicated in genetically complex disorders, i.e., those controlled by multiple loci, can hardly be found using this strategy because of the complications associated with multiple loci linkage analysis.

Specialized databases for homology searches have also been utilized in disease gene discovery projects. In recent years a number of efficient sequence comparison tools have been developed such as the BLAST (Basic Local Alignment Search Tool) family of programs designed for comparison of a single "search sequence" with a database (see Altschul et al., 1990, J. Mol. Biol. 215:403–410; Altschul et al., 1997, Nucleic Acids Res. 25:3389–3402), the family of Hidden Markov Model methods for comparison of a set of aligned sequences that usually represent a protein motif or domain with a database (e.g., Krogh et al., 1994, J. Mol. Biol. 235:1501–1531; Grundy et al., 1997, Biochem Biophys. Res. Commun. 231:760–6) and various other comparison tools (Wu et al., 1996, Comput. Appl. Biosci 12:109–118; Neuwald et al., 1995, Protein Sci. 4:1618–1632; Neuwald, 1997, Nucleic Acids Res. 25:1665–1677).

When used in disease gene discovery projects, homology searches can be enhanced by creating specialized databases that utilize statistical analysis for evaluating significance of sequence similarities in comparison of new sequences with a database of known sequence. Such databases are fine-tuned to the size of the database used (Altschul et al., 1990, J. Mol. Biol. 215:403–410; Altschul et al., 1997, Nucleic Acids Res. 25:3389–3402), so that the same level of homology between a search sequence and a database sequence can be determined to be highly significant if the search sequence is compared with a smaller database, or insignificant and thus undetectable, if the search sequence is compared with a larger database.

In alternatives to standard homology searches, in projects oriented towards gene discovery, researchers usually have some a priori knowledge about the set of genes/proteins that might display important similarity to the unknown new gene. Therefore, selecting an a priori defined set of genes/proteins for comparison with new experimental sequences is a feasible and useful strategy. This strategy was successfully applied to search for homologs of disease genes in yeast and nematode genomes by Mushegian et al. (1997, Proc. Natl. Acad. Sci USA 94:5831–5836).

Two homologous genes taken from different species that originate from the nearest common ancestor by speciation are referred to as orthologs, while any two genes that originate from a common ancestor via a series of events involving intragenomic duplications are call paralogs. Tatusov et al. (1994, Proc. Nat.l, Acad. Sci USA 91:12091–12095) describe comparisons of proteins encoded by the genomes of different phylogenetic lineages and elucidation of consistent patterns of sequence similarities permitting the delineation of clusters of orthologous groups (COGs). Each COG consists of individual orthologous genes or orthologous groups of paralogs from different phylogenetic lineages. Since orthologs typically have the same function, the classification of known genes and proteins into clusters of orthologous groups permits the assignment of a function to a newly discovered gene or protein by merely classifying it into a COG. Although Tatusov describes a method for assigning a function to a newly discovered gene, he does not describe a method for predicting the existence of undiscovered genes. In addition, Yuan, et al. attempted simultaneous reconstruction of a species tree and identification of paralogous groups of sequences and detection of orthologs in sequence databases (Yuan et al., 1998, *Bioinformatics* 143:285–289).

Other groups have aimed at capturing interactions among molecules through the use of programs designed to compare structures and functions of proteins (Kazic 1994, In: *Molecular Modeling: From Virtual Tools to Real Problems*, Kumosinski, T. and Liebman, M. N. (Eds.), American Chemical Society, Washington, D.C. pp. 486–494; Kazic, 1994, In: *New Data Challenges in Our Information Age* Glaesar, P. S. and Millward, M. T. L. (Eds.). Proceedings of the Thirteenth International CODATA Secretariat, Paris pp. C133–C140; Goto et al., 1997, Pac. Symp. Biocomput. p. 175–186; Bono et al., 1998, Genome Res. 8:203–210; Selkov et al., 1996, Nucleic Acids Res.24:26–28). These projects are significantly different from the inventive methods described herein because they do not describe methods for deducing the existence of as yet unknown genes based on comparisons of regulatory pathways and gene structure between one or more species. The present invention provides a method for increasing the sensitivity of analysis methods through the generation of specialized databases.

3. SUMMARY OF THE INVENTION

In accordance with the present invention there is provided methods for identification of novel genes comprising (i) generating one or more specialized databases containing information on gene/protein structure, function and/or regulatory interactions; and (ii) searching the specialized databases for homology or for a particular motif and thereby identifying a putative novel gene of interest. The invention may further comprise performing simulation and hypothesis testing to identify or confirm that the putative gene is a novel gene of interest.

The invention is based, in part, on the observation that functionally similar regulatory systems are generated during evolution by genetic duplication of ancestral genes. Thus, by comparing phylogenetic trees or regulatory networks and identifying genes and/or proteins absent in one system under comparison, the existence of as yet unidentified genes and/or proteins can be predicted. To make meaningful comparisons of phylogenetic trees it is necessary to distinguish between orthologs and paralogs. The present invention provides a method useful for discriminating between orthologs and paralogs and inferring the existence of as yet unidentified genes and/or proteins.

In accordance with the present invention, specialized databases are developed that contain information on gene/ protein structure and interactions based on information derived from preexisting databases and/or research articles including information on interactions among genes and proteins, their domain/motif structure and their subcellular and tissue expression/distribution patterns.

The invention relates to a sequence analysis program which utilizes the specialized database for comparison of a single sequence, processing the output into a sequence alignment, computing phylogenetic trees, and analyzing these trees to predict undiscovered genes. This program also includes a set of tools for generating motif/domain models from multiple sequence alignments of known genes and for using these models for extraction of structurally and/or functionally homologous sequences from databases which contain raw sequence data.

The invention further provides for a simulation and hypothesis testing program which relies on the specialized databases of gene/protein interactions for identifying potentially undiscovered members of multigene families through comparisons of regulatory networks for different species and testing hypotheses with regard to regulatory cascades. A comparison of homologous regulatory networks within the same organism and between different species of organisms will allow the identification of genes absent in one of the systems under comparison, thus providing a set of candidate genes. In this way, genes that contribute to the phenotype of a specific disease associated with a particular biological system under analysis may be identified, mapped and subjected to mutational analysis and functional studies.

4. BRIEF DESCRIPTION OF THE DRAWINGS

FIG. 3 shows a set of keywords defining proteins involved in apoptosis pathways, these keywords having been utilized for generating a specialized sequence database Apoptosis3, this list having been compiled manually for testing the concept of specialized databases;

Figure 4:
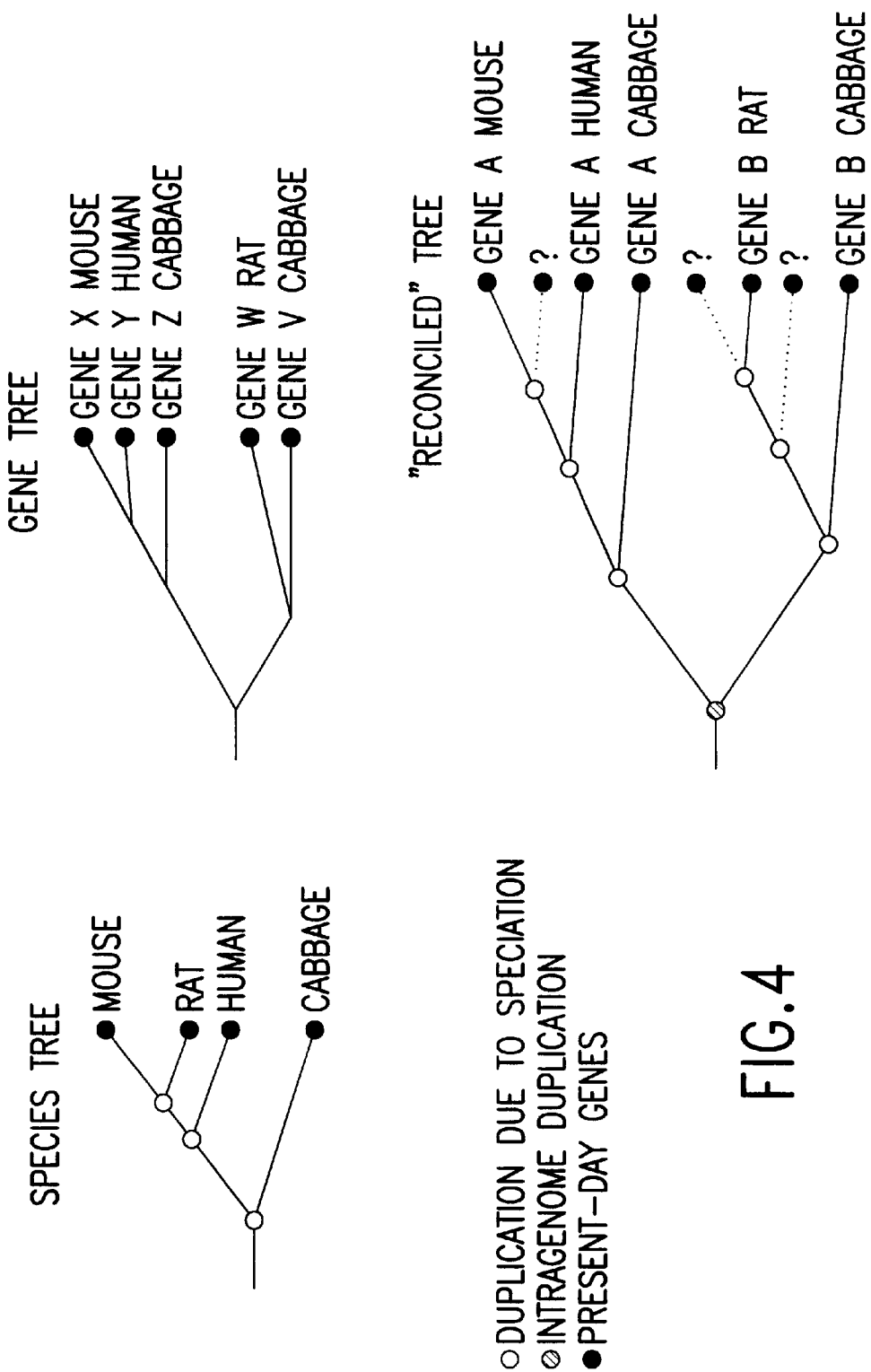
Figure 5A:
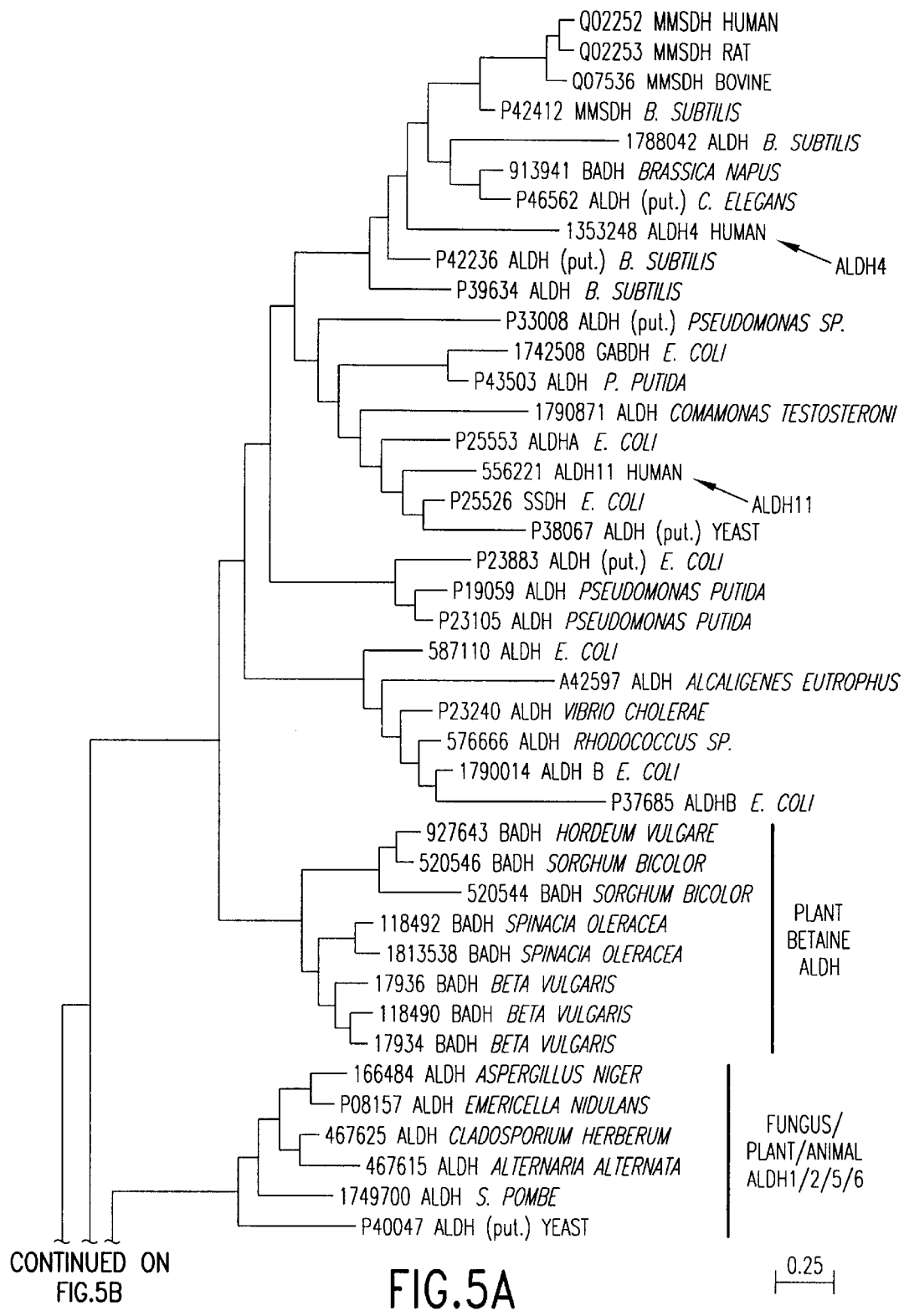
Figure 5B:
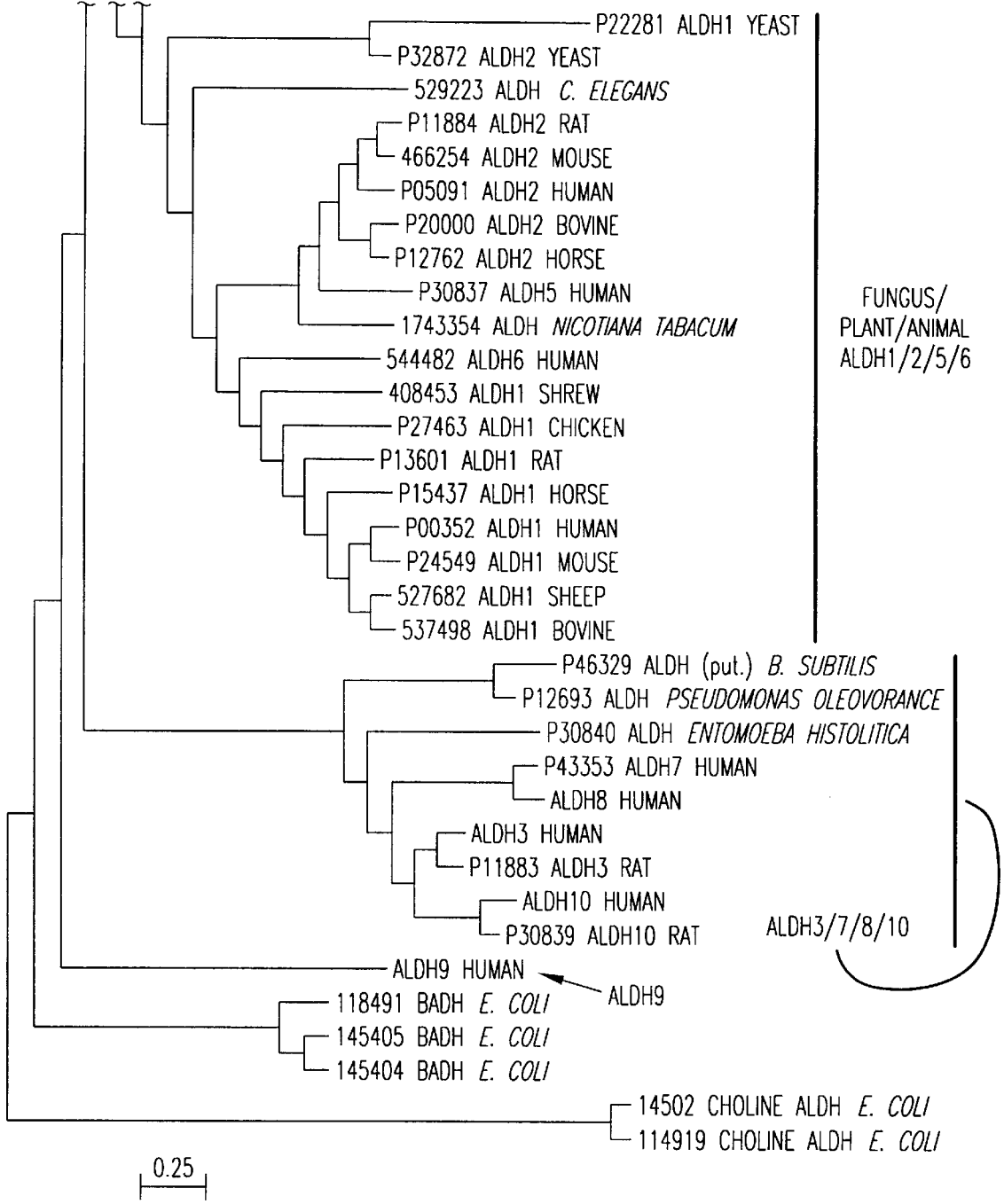
Figure 6A:
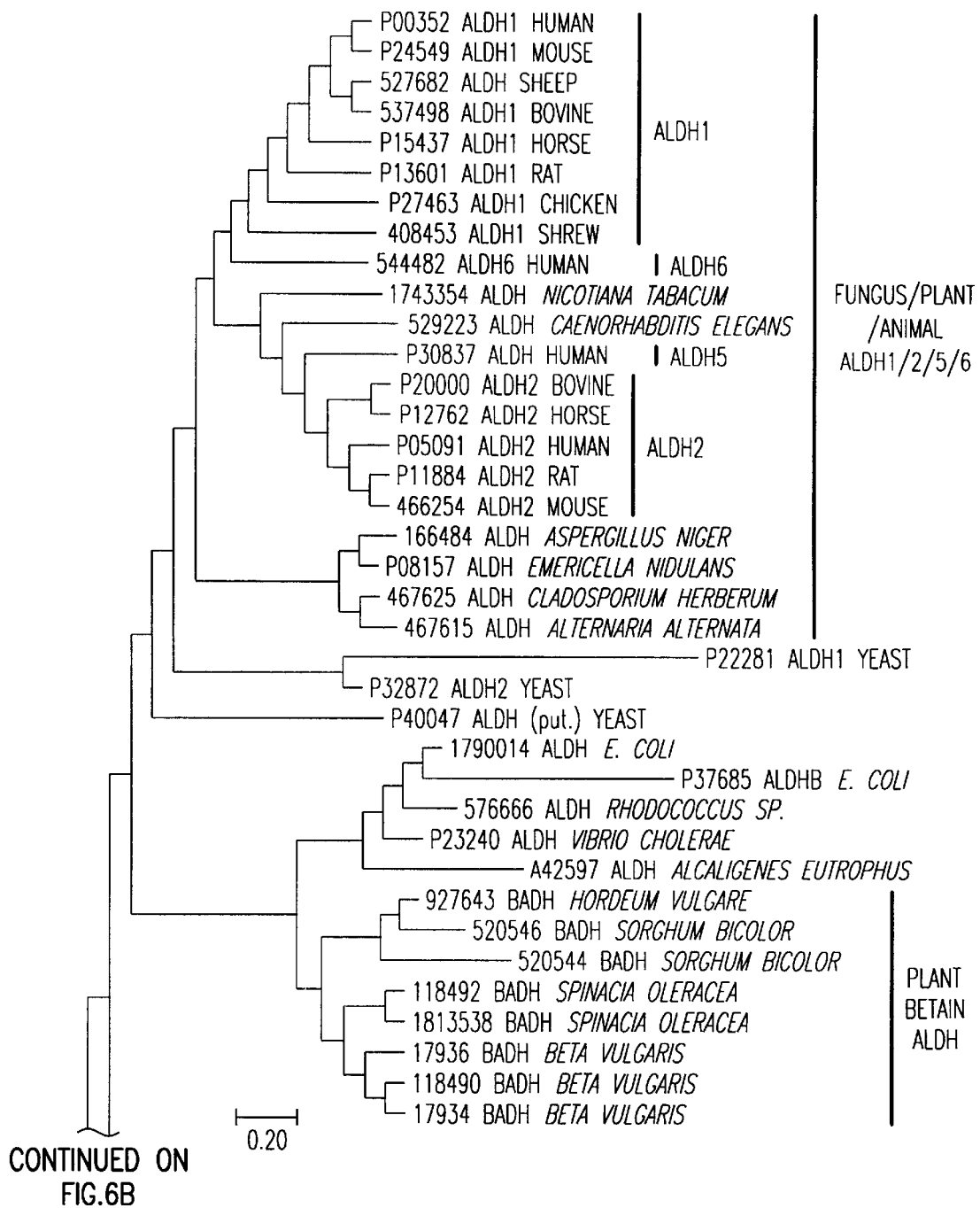
Figure 6B:
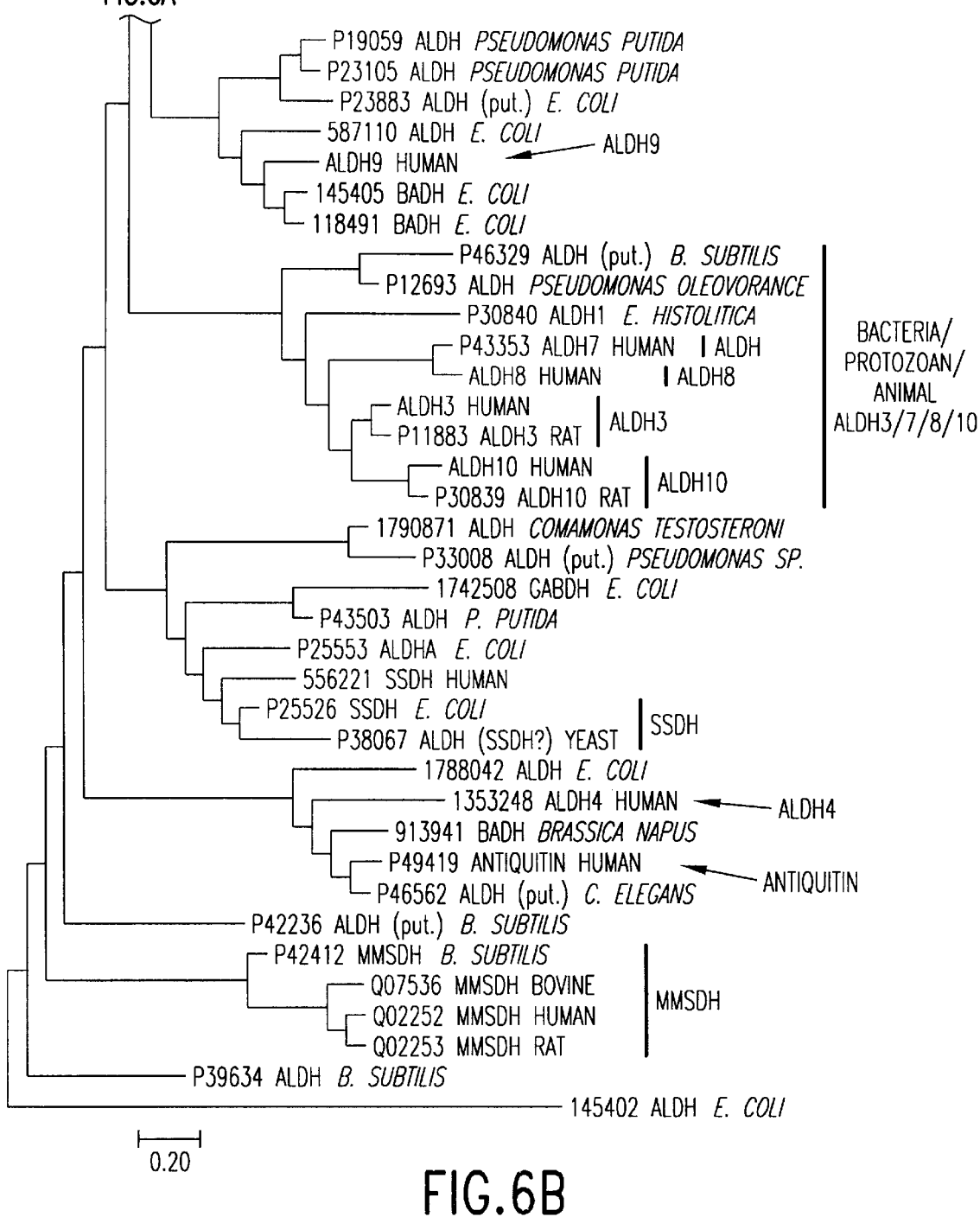
Figure 7:
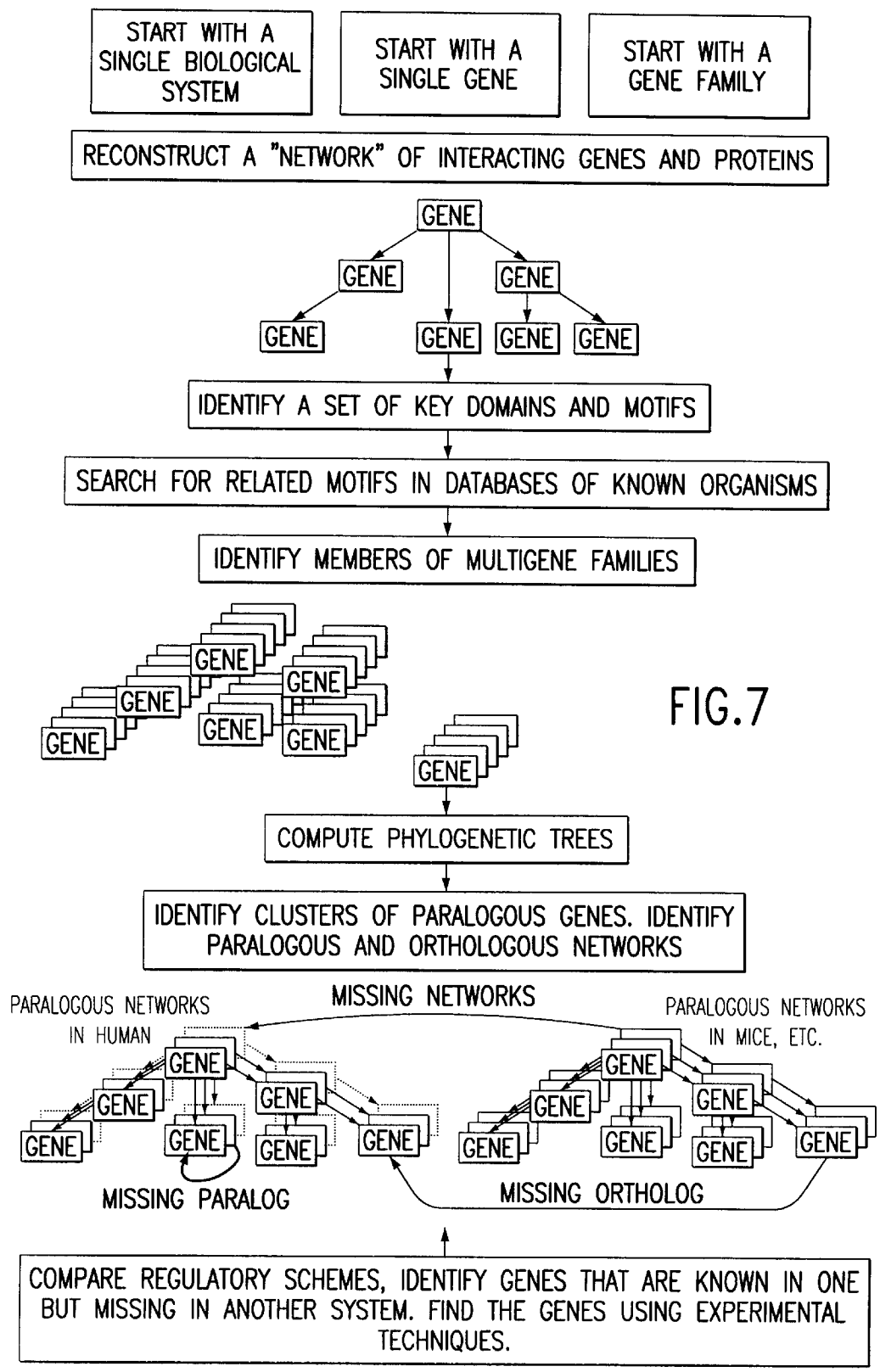
Figure 10A:
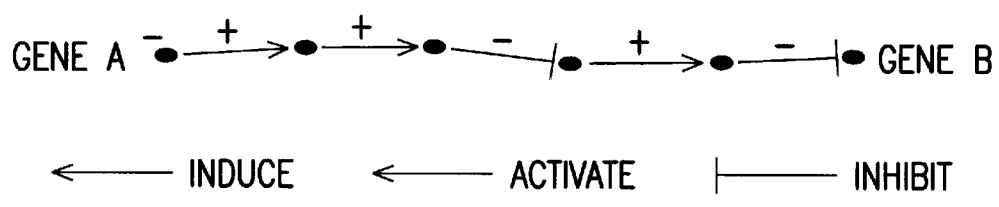
Figure 10B:
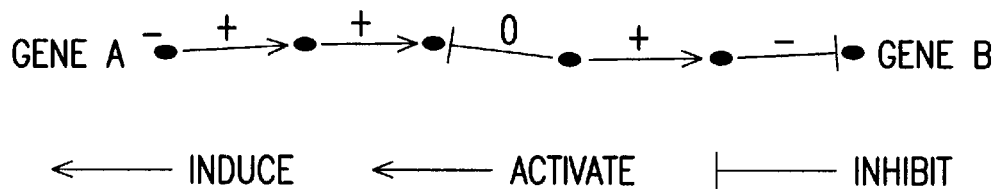
Figure 11:
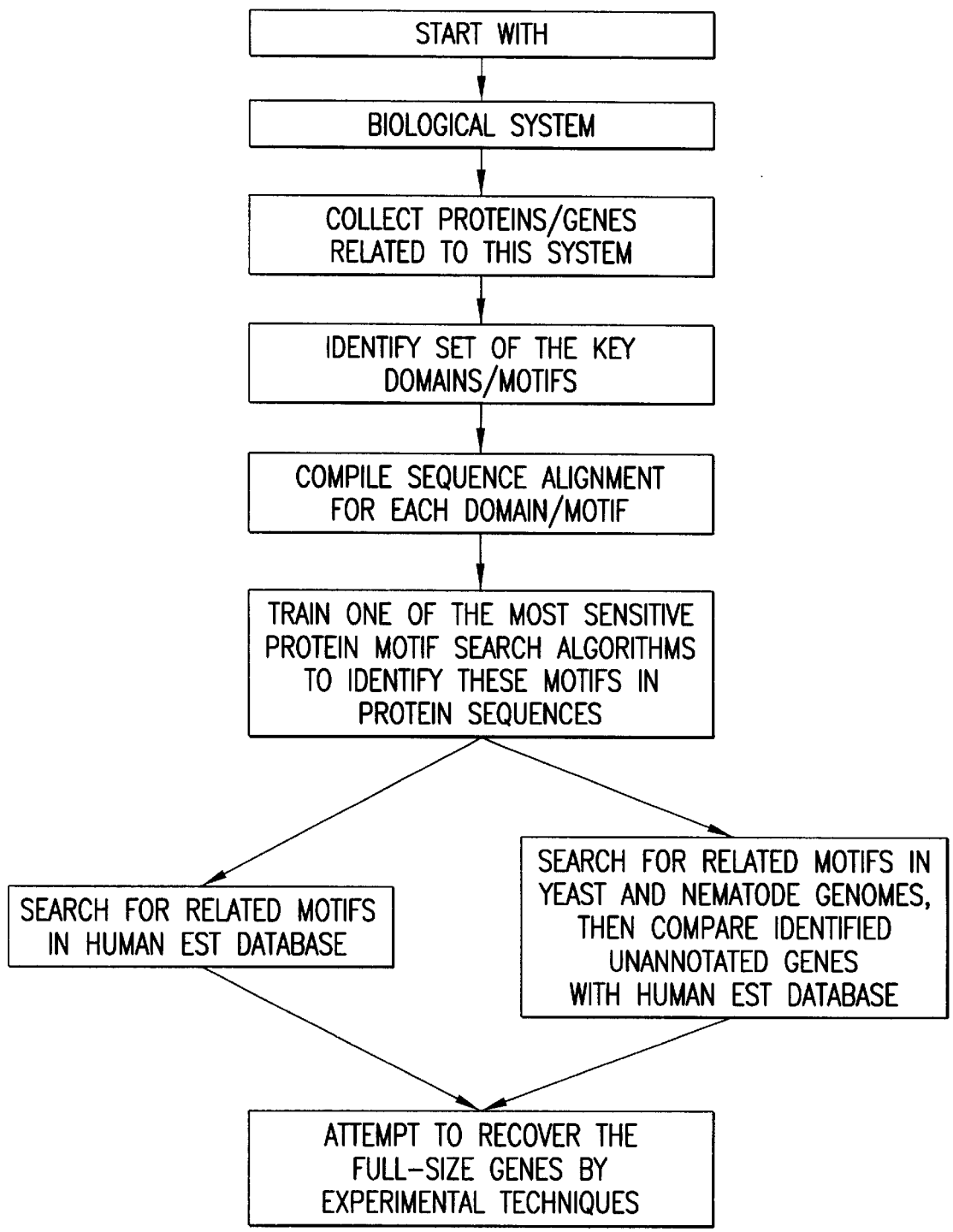
Figure 12B:
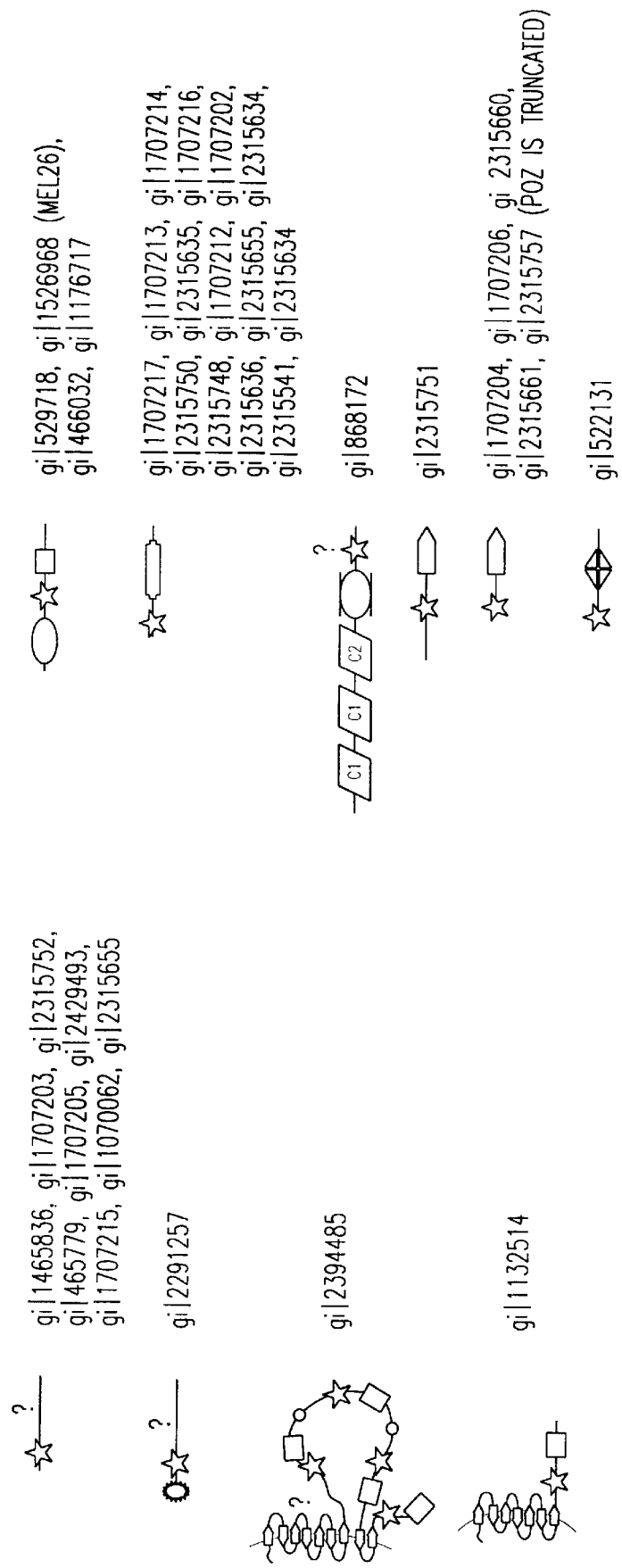
Figure 12C:
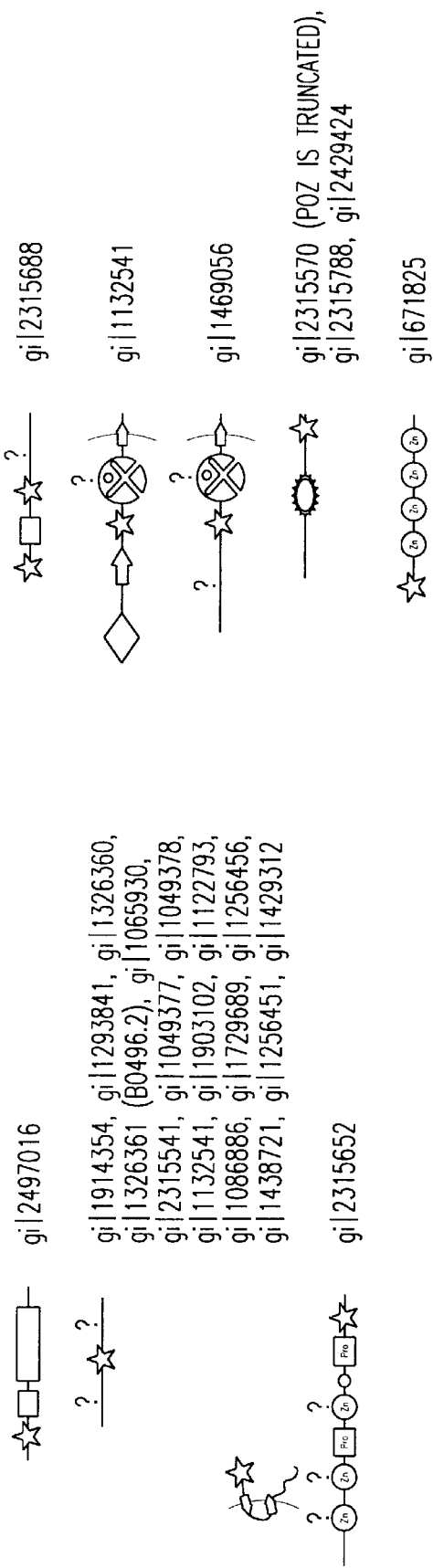

FIG. 4 shows a "species tree," which is a graph depicting the correct order of speciation events leading to a set of present day species; a "gene tree," which is a graph depicting a history of a few genes from the same species, where each species can be represented by multiple paralogous genes (because the set of known genes is incomplete for most genomes, and there are often multiple representations of the same gene family in the same genome, the gene tree can be drastically different from the corresponding species tree); and a "reconciled tree", which is the gene tree that would be obtained if gene deletions were completely forbidden and all genes were known for all species under analysis;

FIG. 5 shows the original tree of ALDH sequences, indicating sequence clusters where bacterial, plant, fungal and nematode orthologous genes are present, but a human ortholog was not yet known;

FIG. 6 shows the same phylogenetic tree as in FIG. 5 with an additional human protein, referred to as antiquitin which was discovered by the method of the invention;

FIG. 7 is a schematic diagram illustrating functional network-based gene discovery in accordance with the present invention;

FIG. 8 presents diagrams depicting the regulatory relationships among hypothetical proteins (denoted with Arabic numerals) of hypothetical species A and B. Proteins in different species denoted with the same numeral are considered orthologous. The diagrams show that regulatory relationships between a pair of proteins can be of three different kinds;

FIGS. 8B, 8C, and 8D are diagrams representing Boolean operations OR, AND, and XOR, on arcs of the two oriented graphs of FIG. 8A, the same operations being applicable to the set of vertices of the two oriented graphs;

FIG. 9 is a diagram representing a hypothetical example of defining homologous protein networks in two different species using protein motifs, the diagram showing only two hypothetical proteins (1 and 2) for species A and three hypothetical proteins (1, 3, and 4) for species B. Protein 1 in both species has motifs α and β, protein 2 has motifs δ, ε, and ζ, and proteins 3 and 4 have motifs δ and ζ, and ε, respectively. The motif analysis can indicate that proteins 3 and 4 in species B may collectively perform the same function as protein 2 in species A;

FIGS. 10A and 10B are diagrams respectively representing hypothetical examples of evaluating the impact of a "knockout" of hypothetical gene A on the expression of a hypothetical gene B. The effect of knock-out of gene A calculated by multiplication along the shortest pathway connecting genes A and B is inhibition of gene B, the resulting effect being zero if the orientation of only one arc in the same pathway is reversed;

FIG. 11 is a flow chart representing the scheme of gene discovery analysis involving motif/domain analysis in accordance with the present invention; and FIG. 12. Identification of genes in *C. elegans* containing either POZ or kelch domains. The protein excession numbers are indicated adjacent to the different protein domains. The protein corresponding to accession number gi/1132541 contains a POZ domain, death domain, kinase domain and heat repeat.

FIG. 13A. Two human sequences with the closest homology to the *C. elegans* sequence gi/1132541 (SEQ ID NO:1, SEQ ID NO:2).

Figure 13B:
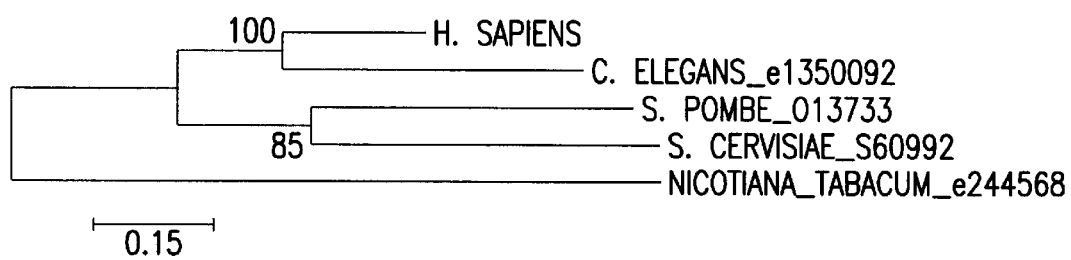

FIG. 13B. Computed gene tree indicating that the identified human gene represents an ortholog of the *C. elegans* gene gi/1132541.

FIG. 13C. Nucleotide sequence of the death domain gene (SEQ ID NO:3).

Figure 13D:
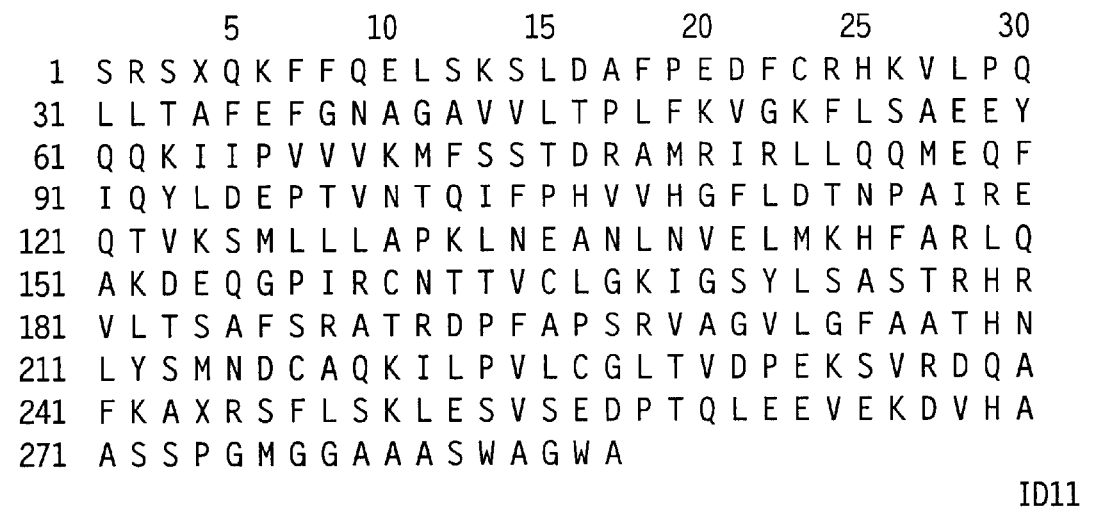

FIG. 13D. Deduced amino acid sequence of the death domain protein (SEQ ID NO:4).

FIG. 14. Identification of candidate gene implicated in the etiology of Chronic Lymphocytic Leukemia (CLL). Sequence homology between a CLL region open reading frame and mouse Rpt1 (sp/P15533/RPT1) is presented (SEQ ID NO:5 and SEQ ID NO.6).

FIGS. 15A–B. Model of regulatory functions of Rpt1. FIG. 15A indicates that in mouse T lymphocytes Rpt1 serves as a repressor of the gene for interleukin 2 receptor (IL-2R). FIG. 15B demonstrates that when Rpt1 is knocked out, the regulatory effect is manifested as a block of the apoptotic pathway for T-lymphocytes resulting in accumulation of T-lymphocytes in blood.

FIG. 16A. Two EST sequences identified by searching a protein dbEST using the mouse Mad3 protein as a query (SEQ ID NO:7, SEQ ID NO:8, SEQ ID NO:9, SEQ ID NO:10).

FIG. 16B. Nucleotide sequence of the human Mad3 gene (SEQ ID NO. 11).

FIG. 16C. Complete sequence of the human Mad3 protein (SEQ ID NO. 12). A search was conducted to identify overlapping sequences. The complete sequence of the gene was assembled and the amino acid sequence deduced. The translated human Mad3 sequence consists of 206 amino acid residues 81% of which are identical to the mouse Mad3 protein.

FIG. 16D. Multiple alignment of the human Mad3 amino acid sequence with known Mad proteins (SEQ ID NOS: 13–18).

Figure 17A:
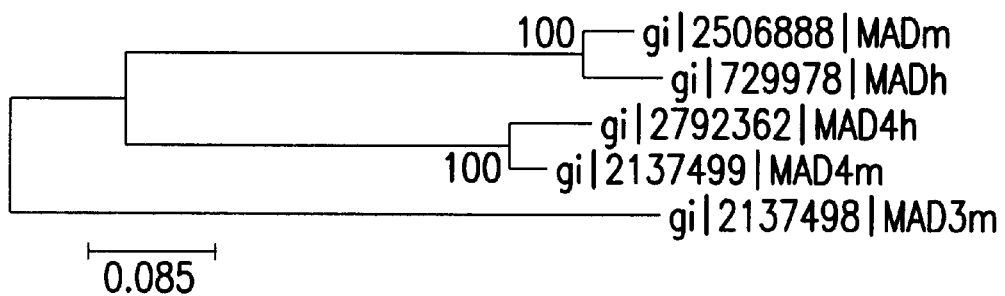

FIG. 17A. Phylogenetic tree indicating relationship between three known mouse Mad genes and their two human homologs.

Figure 17B:
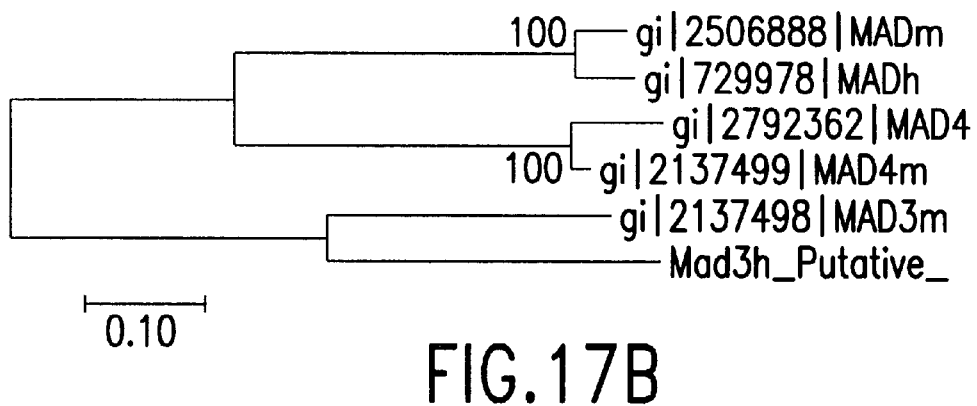

FIG. 17B. Phylogenetic tree including new human Mad3 sequence. The phylogenetic tree indicates that the new human gene belongs to the family of Mad proteins and is an ortholog of mouse Mad3.

5. DETAILED DESCRIPTION OF THE INVENTION

The present invention provides methods for identification of novel genes comprising: (i) generating specialized databases containing information on gene/protein structure, function and regulatory interactions and, (ii) sequence analysis which includes homology searches and motif analysis thereby identifying a putative novel gene of interest. The invention may further comprise performing simulation and hypothesis testing to identify or confirm that the putative gene is a novel gene of interest.

The specialized databases are constructed utilizing information concerning gene/protein structure or function derived from unpublished data, research articles and/or existing databases. The specialized databases can be used to identify novel genes by: (i) searching for motif/domain combinations characteristic for a putative gene of interest; (ii) phylogenetic tree analysis of homologous genes for predicting the existence of yet undiscovered genes; (iii) comparing members of interactive gene/protein networks from different species for predicting the existence of yet undiscovered genes; and (iv) testing a hypothesis with regard to known interactions of homologs from other species in regulatory pathways.

5.1. Generation of Specialized Databases

In accordance with the present invention, specialized databases may be developed that contain information derived from unpublished data, research articles and/or databases concerning interactions among genes and proteins, their domain/motif structure, and their biological functions.

For example, but not by way of limitation, a specialized database may be prepared as follows. Protein and gene sequences may be provided, for example, by the Java program PsiRetrieve which allows for quick retrieval of protein or nucleotide sequences from binary BLAST databases by sequence accession number, keyword or groups of keywords, or species name. In addition, using the program PsiRetriever, sequences encoding the proteins of interest may be retrieved from the non-redundant (NCBI) database of protein sequences and stored as a FASTA file. The FASTA file is then converted into a binary blast database using the program FORMATDB from the BLAST suit of programs.

Known motifs/domains for proteins may also be collected using the flat file versions of major protein databases, such as SwissProt and the non-redundant database of NCBI. The databases can be downloaded and searched for the keywords "motif" and "domain" in the feature tables of proteins. In addition, existing databases of motifs and domains, such as BLOCKS and pfam, can be downloaded (Henikoff et al., 1991, NAR 19:6565–6572). Still further, it is understood that any publicly available database containing gene/protein sequences may be utilized to generate the specialized databases for use in the practice of the present invention.

Homologous sequences may be aligned using, for example, the CLUSTALW program (Higgins, et al. 1996 Methods in Enzymology 266:383–402). A protein's sequence corresponding to each domain/motif can be identified, saved and used for building a Hidden Markov Model (HMM) of the domain/motif using a HMMER and HMMER2 packages (see, Durbin, R. et al. 1998 in Biological Sequence Analysis: Probablistic Models of Proteins and Nucleic Acids). HMMER and HMMER2 packages are useful for (i) building HMMs from sets of aligned protein or nucleotide sequences, and (ii) comparing the HMMs with sequence databases aimed at identifying significant similarities of HMMs with database sequences. Both nucleotide and protein databases can be used for this purpose. Alternatives to the Hidden Markov Model method for building domain/motif models include neural network motif analysis (Wu, C. H. et al., 1996, Comput Appl Biosci 12, 109–18; Hirst, J. D., 1991, Protein Eng 4:615–23) and positional weight matrix analysis (Claverie, J. M., 1994, Comput Chem 18:287–94; Venezia, D., 1993, Comput Appl Biosci 9:65–9; Bucher, P. 1996, Comput Chem, 20:3–23; Tatusov, R. L., 1994, Proc Natl Acad Sci USA 91:12091–5).

Once a comprehensive collection of motifs/domains is created, each particular protein may be compared against a complete database of HMMs to identify known motifs and domains.

The Hidden Markov Model (HMM) is built using the following steps:

A1. Start with a motif/domain name and a single amino acid sequence representing a domain or motif.

A2. Do PSI-BLAST (BLASTPGP) search with the motif/domain sequence against a protein non-redundant database.

A3. Retrieve the sequences identified in the database search from the protein sequence database. Exclude low-complexity sequences, short or incomplete sequences and sequences with similarity score above a selected threshold of PPD value <0.001

A4. Align the set of sequences with CLUSTALW (or other multiple sequence alignment program).

A5. Use the set of aligned sequences for building HMM with the programs provided with HMMER and HMMER2 packages (see Hughey and Krogh 1996, J. Mol. Biol. 235:1501–1531).

A6. Do a new database search comparing new HMM with the non-redundant protein database.

A7. Continue steps A3–A6 until the convergence of the Markov model i.e., until no new sequences are identified, or the maximum allowed number of iterations as defined by the user is reached. (Hugh R. and Krogh A., 1996, Comput. Appl. Biosci. 12:95–107).

Figure 1:
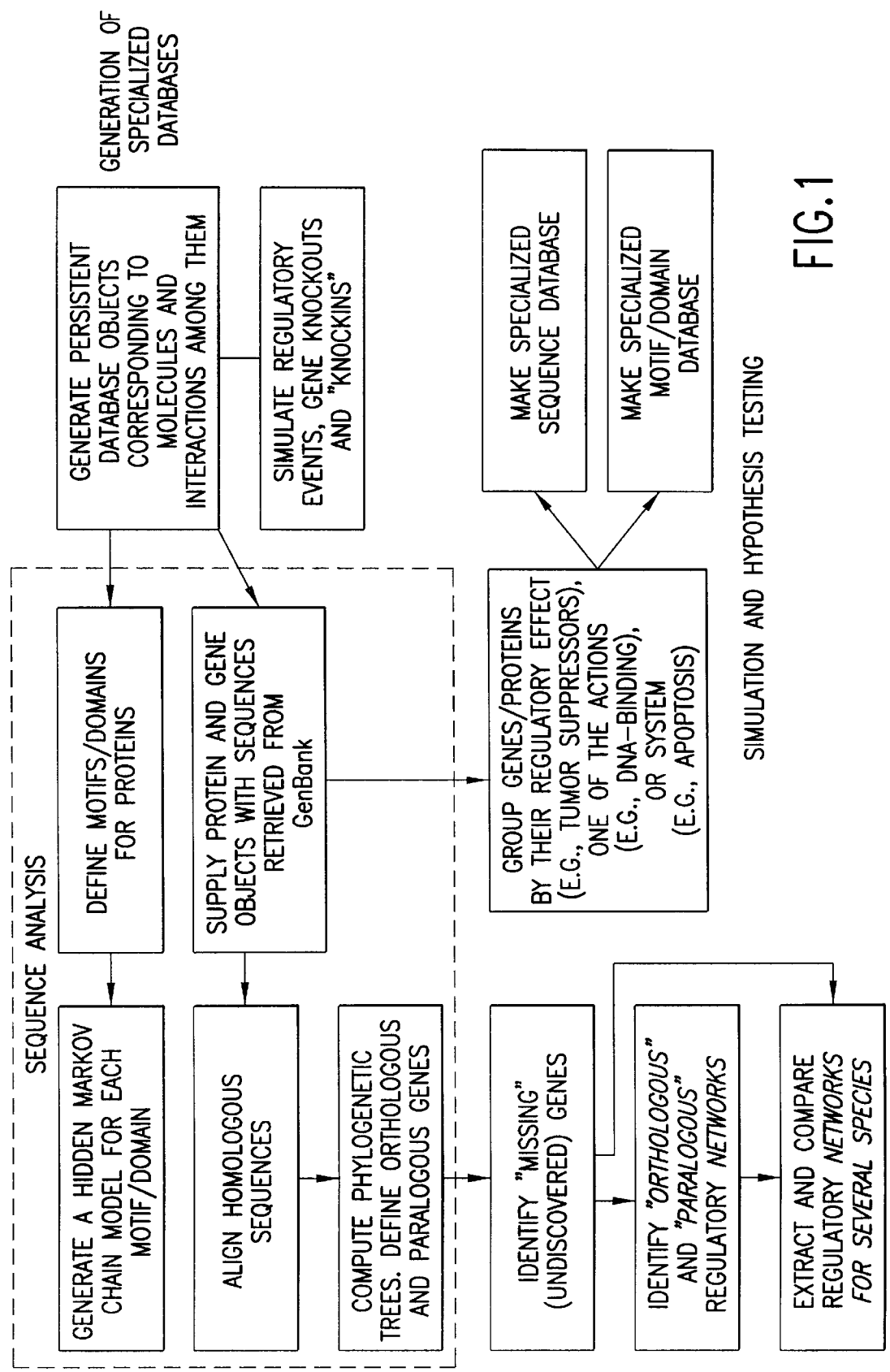
FIG. 1 is a block diagram illustrating the three major programs of the method according to the present invention: (i) the generation of specialized databases based on information on gene/protein structure, function and regulatory interactions derived from research papers and databases; (ii) sequence analysis; and (iii) simulation and hypothesis testing.
Figure 2A:
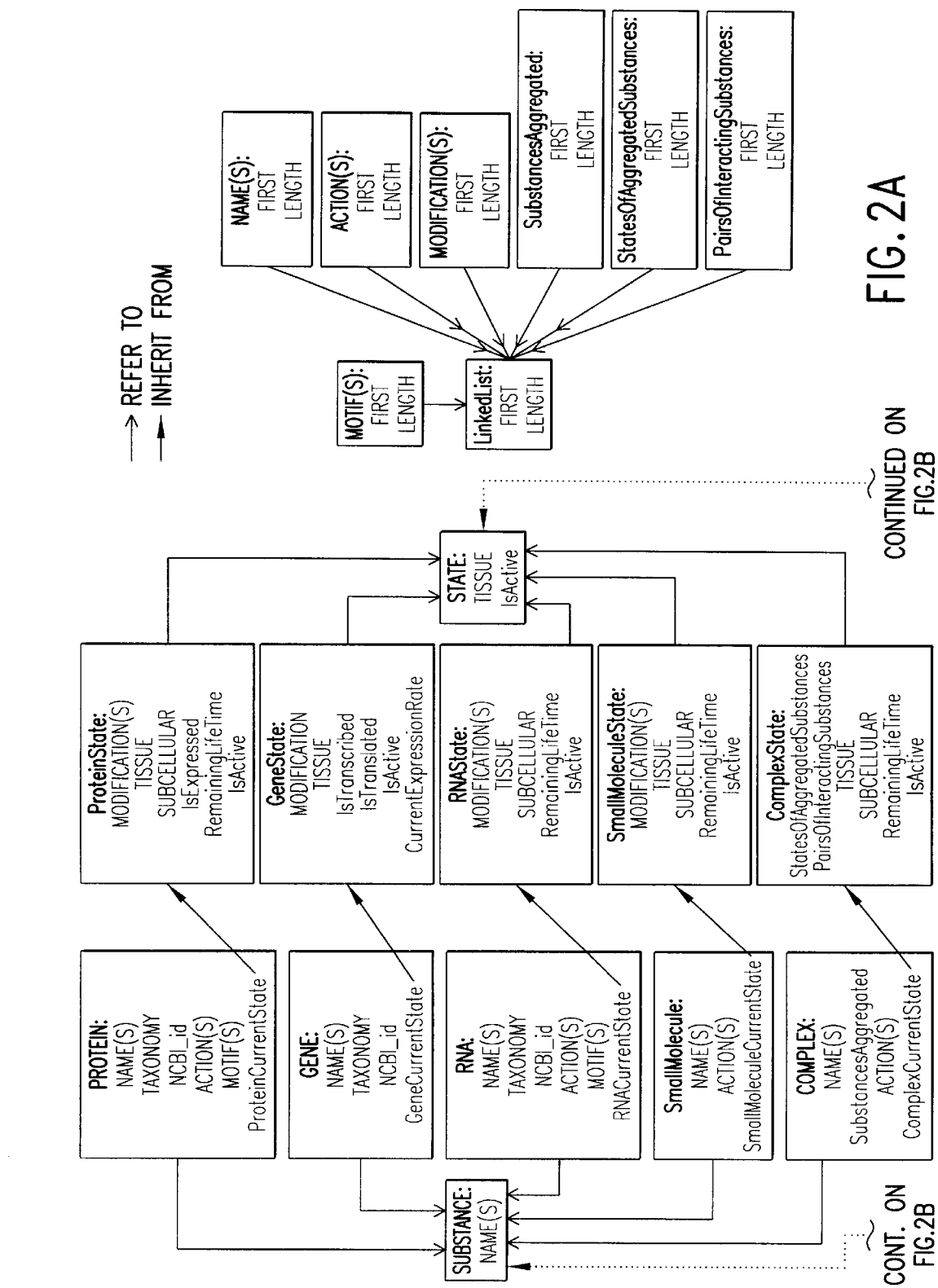
FIG. 2 is a diagram illustrating the object representation of molecules and relations between them.
Figure 2B:
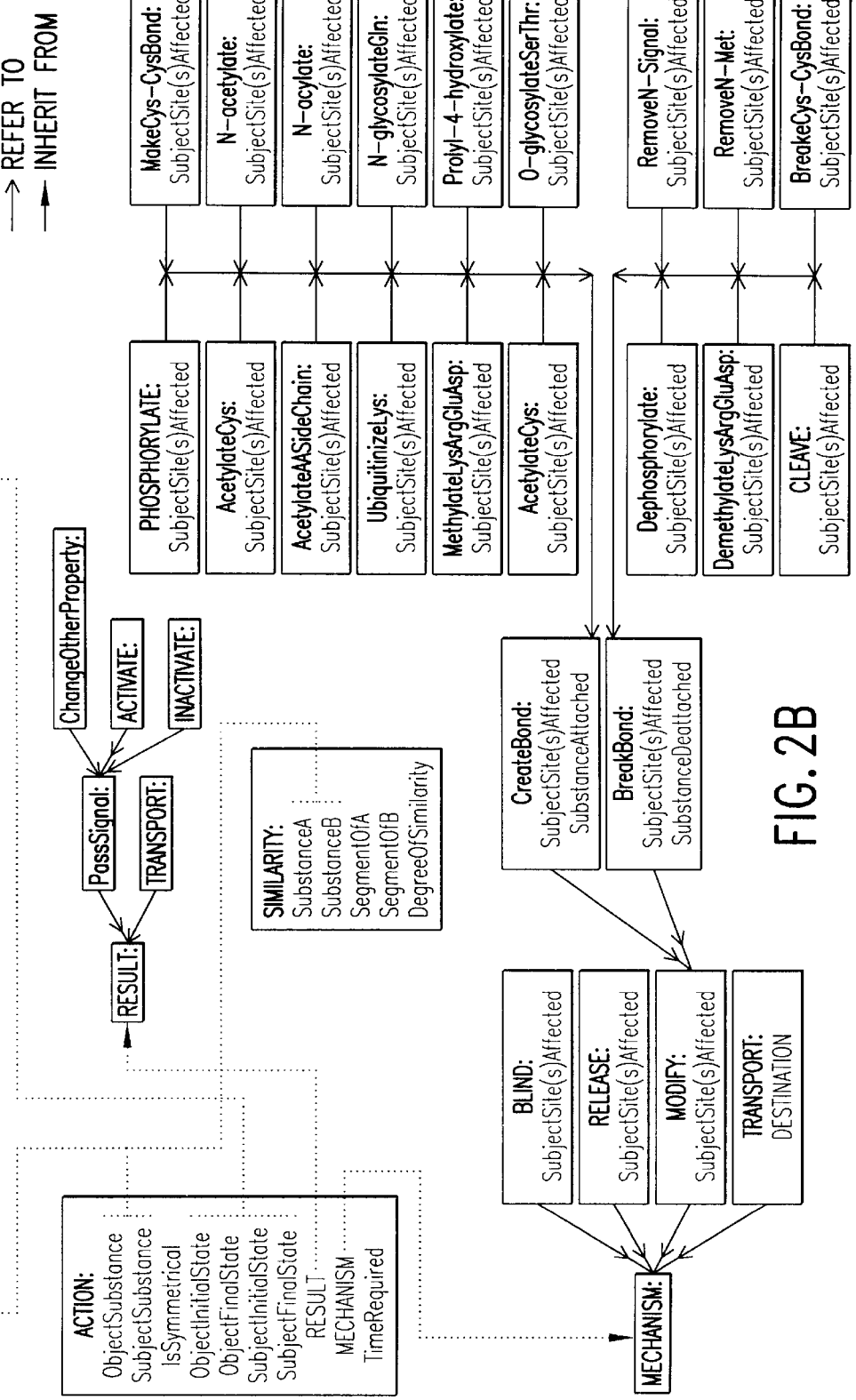

In addition, in yet another embodiment of the invention, a specialized database may be designed to contain a semantic model of proteins and of the possible interactions between them. Such databases are particularly useful for computation and analysis of regulatory networks between proteins. The semantic model is designed for representing substances, such as proteins and actions between them, and is based on widely accepted principles of object-oriented programming languages such as Java. FIG. 2 is a diagram illustrating the object representation of molecules and relations between them. As indicated in FIG. 2 there are six major classes, corresponding to the top-level classification of objects and actions: (i) a substance; (ii) a state of a substance; (iii) a similarity between substances; (iv) an action between substances; (v) a result of the action; and (vi) a mechanism that enables an action.

FIG. 2 presents the class design graphically, listing the variables that represent the properties of each class or class object in the implementation. Classes can be made nested via the mechanism of "inheritance", i.e., classes are defined starting with the most general ones and moving towards more specific classes. Definition of more specific classes is simplified because the properties of the general classes are "inherited" by the specific classes and need not be redefined each time (see, Flanagan 1997, Java in a Nutshell, Second Edition. O'Reilley & Associates, Inc. Sebastopol, Calif.).

As shown in FIG. 2, the two key object types in this scheme are substances (nodes of the graph representing regulatory networks) and actions (oriented edges connecting pairs of nodes), while result and mechanism objects are auxiliary to object action. Each substance object is characterized with a state. In this scheme, action is the most complicated object; each action object is characterized by a specific pair of substances participating in the action, one of which can be active and is referred to as Subject Substance and the second of which can serve as a substrate for the former and is referred to as Object Substance. Furthermore, for each action the initial and final states corresponding to interacting substances are defined. The property Time Required of each Action Object allows the setting of different durations for different actions (time is measured in relative units; see René Thomas and Richard D'Ari, 1990, "Biological Feedback," CRC Press Boca Raton, Ann Arbor, Boston).

Once developed, the specialized databases can be used to identify novel genes based on computation and analysis of phylogenetic trees for multigene families and analysis of homologous regulatory networks.

In a specific embodiment of the invention, a specialized database was generated using a set of keywords defining proteins involved in apoptosis (see, FIG. 3). The specialized sequence database was referred to as Apoptosis 3. As a first step in generating the specialized database, a comprehensive set of articles describing the system of apoptosis or programed cell death was compiled. The articles were analyzed and information on regulatory pathways characterizing apoptosis from a variety of different organisms was extracted. Such pathways included those involved in MHC-T cell receptor interactions, inflammatory cytokine signal transduction, induction by light, γ-radiation, hyperosmolarity or heat shock, pathways involving immunoregulatory receptors or receptors having cytoplasmic domains, integrin-related pathways and perforin/granzymeβ related pathways. The collected information was stored using Powerpoint (Microsoft) as a collection of graph/plots depicting the regulatory pathway. In addition, a list of proteins relevant to regulation of apoptosis was compiled.

Using the program Psi Retriever, sequences encoding the proteins relevant to regulation of apoptosis were retrieved from the non-redundant (NCBI) database of protein sequences and stored as a FASTA file. The FASTA file was then converted to a binary blast database using the program FORMATDB from the BLAST suit of programs. The BLAST suit of programs provides a set of programs for very fast comparisons of a single sequence to a large database. Both the database and the search or query sequence can be any combination of nucleotide and/or amino acid sequences.

In a working example described herein, the Apoptosis 3 database was used to compare genomic and cDNA sequences derived from the 13 q region of human chromosome 13. This region of the chromosome is associated with Chronic Lymphocytic Leukemia (CLL). Using this method of analysis a human gene with significant homology to the mouse Rpt1 gene was identified. When the activity of Rpt1 is knocked out in mice, the regulatory effect is manifested as a block in T-lymphocyte apoptosis. This result indicates that the identified human Rpt1 homology may represent the gene in which genetic defects lead to CLL.

The amino acid sequence of the human Rpt1 gene is presented in FIG. 14. The present invention relates to nucleic acid molecules encoding the human Rpt1 protein shown in FIG. 14. The invention also relates to nucleic acid molecules capable of hybridizing to a nucleic acid molecule encoding the human Rpt1 protein presented in FIG. 14 under conditions of high stringency. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH7.5), ImM EDTA, 0.02% PVP, 0.02% Ficoll, 0.02% BSA and 500 mg/ml denatured salmon sperm DNA. Filters are hybridized for 48 h at 65° C. in prehybridization mixture containing 100 mg/ml denatured salmon sperm DNA and 5–20×10$^6$ CpM of $^{32}$P-labeled probe. Washing of filters is done at 37° C. for 1 h in a solution containing 2×SSC, 0.01% PVP, 0.01% Ficoll and 0.01% BSA. This is followed by a wash in 0.1×SSC at 50° C. for 45 minutes before autoradiography. Other conditions of high stringency which may be used are well known in the art.

5.2. Gene Discovery Through Phylogenetic Analysis of Gene Families

The present invention provides a method for identifying novel genes comprising the following steps: (i) comparing a single sequence with a database; (ii) processing the output into a sequence alignment; (iii) computing gene trees; and (iv) analyzing the trees to predict the existence of undiscovered genes.

FIG. 4 shows a "species tree," a "gene tree" and a "reconciled tree". A "species tree", as defined herein, is a graph depicting the correct order of speciation events leading to a set of present day species as defined by taxonomy. A "gene tree" is a graphical representation of the evolution of a gene from a single ancestral sequence in a common progenitor to a set of present-day sequences in different species. Where gene duplication has occurred, a branch is bifurcated. The branch lengths of a gene tree are most frequently measured either in terms of the number of amino acid or nucleotide replacements per site or in terms of millions of years (absolute geological time). In the former case, the average replacement rate in the majority of the published trees varies among tree branches, and the root-to-tip distances are different for different present day sequences. In the latter case, all root-to-tip distances are equal and the height of each interior node of the tree corresponds to the absolute geological time passed since the gene duplication corresponding to the interior node took place.

If a gene is unique, i.e., represented with a single copy per genome rather than being a member of a family of similar genes, the correct gene tree depicting the origin of this gene in a few different species is identical to the species tree. In many instances, a single ancestral gene has been duplicated repeatedly during evolution to form a multigene family. A gene tree is constructed from a gene as it occurs in several species and reflects both speciation events and gene duplications within the same genome. Two homologous genes taken from different species that originated from the nearest common ancestor by speciation are referred to as orthologs, while any two genes that originated from the common ancestor via a series of events involving intragenomic duplications, or conversions, are called paralogs. The terms "ortholog" and "paralog" are applied to both nucleic acid and proteins herein.

If gene deletions are forbidden and all genes for all species represented in the tree are known, the gene tree can be reconfigured to recapitulate the species tree, such that each subtree contains only orthologous genes. This tree is referred to as a reconciled tree and is shown in FIG. 4. Imperfect gene trees which contain incorrect or partial species subtrees can be used to build reconciled trees that indicate events of speciation, gene loss, and gene duplication.

Orthologs from different species in gene trees are usually clustered together, so that if all the existing homologous genes from different species were known, the same relationship of species would be recapitulated in each cluster of orthologous genes. Since in reality a considerable number of genes are not yet identified, the real gene trees contain incomplete clusters of orthologs that can be used for identification of the missing genes.

By applying phylogenetic analysis, i.e., reconstruction of gene trees of gene/protein sequences, one can predict the existence of undiscovered genes in humans and other species in addition to identifying the function of a gene. Such a technique is a significantly more powerful tool for identification of new genes than mere sequence comparisons.

Methods of computing gene trees from a set of aligned sequences include the: (i) heuristic method based on an optimization principle which is not directly motivated by a probability model (Fitch, 1974 J. Mol. Evol. 3:263–268)), (ii) the maximum likelihood method (Goldman, 1990, Syst. Zool. 30:345–361; Yang et al., 1995, Syst. Biol. 44:384–399; Felsenstein, J., 1996, Methods Enzymol. 266–418–427); and (iii) the distance matrix tree making method (Saito, N. and Nei, M., 1987, Mol. Biol. Evol. 4:406–425). Since the data analyses of orthologs and paralogs often involve very distantly related sequences, the maximum likelihood method is preferably used for small data sets and the distance-matrix method in other instances.

To construct a reconciled tree according to the invention, the first step comprises a search for homologs in a publicly or privately available database such as, for example, GenBank, Incyte, binary BLAST databases, Swiss Prot and NCBI databases. Following the identification of homologous sequences a global alignment is performed using, for example, the CLUSTALW program. From the sequence alignment a gene tree is constructed using, for example, the computer program CLUSTLAW which utilizes the neighbor-joining method of Saito and Nei (1997, Mol. Biol. Evol. 4:406–425). Construction of a species tree is then retrieved from, for example, the database of NCBI.

The species tree and gene tree are given as input into the algorithm described below, which integrates both trees into a reconciled tree. Agreement between the gene tree and the corresponding species tree for any given set of sequences indicates the identification of orthologs. In contrast, disagreement between the species and gene tree suggest a gene duplication that resulted in the formation of a paralog. Thus, through generation of a reconciled tree one can identify orthologs present in one species but missing in another. These can be deduced by forming subtrees of orthologs in a gene tree, and then comparing the subtree in the gene tree with a species tree. A missing gene appears as a branch present in the species tree but absent in the gene tree.

The algorithm for defining an orthologous gene subtree and predicting the undiscovered, or lost in evolution, genes is as follows:

Let $T_g$ be the most likely gene tree identified with one of consistent tree-making methods from a set of properly aligned homologous genes {1, 2, . . . , s}, such that one or more homologous genes from every species corresponds to pending vertices of $T_g$. Each gene is labeled with the species it comes from (1, . . . ,s) adding subscripts to distinguish homologous genes from the same species whenever it is necessary. Let $T_g$ be the true species tree (tree correctly reflecting speciation events which we assume to be known) for species {1, 2, . . . , s}. Due to the biological meaning of $T_s$ each species in this tree is represented only once. It is assumed that both $T_s$ and $T_g$ are binary, although it is straightforward to extend the algorithm described here to the case of multifurcated trees.

Algorithm

A1. For each pair of interior nodes from trees $T_g$ and $T_s$, compute similarity $\sigma(S_{gi}, S_{sj})$.

A2. Find the maximum $\sigma(S_{gi}, S_{sj})$.

A3. Save $S_{gi}$ as a new subtree of orthologs, save $\{S_{gi}\}-\{S_{sj}\}$ as a set of species that are likely to have gene of this kind (or lost it in evolution).

A4. Eliminate $S_{gi}$ from $T_g$; $T_g := T_g \backslash S_{gi}$.

A5. Continue A2–A4 until $T_g$ is non-empty.

The following definitions apply:

Let $S_{gi}$ be an ith subtree of $T_g$ (corresponding to the ith interior node), correspondingly, let $S_{sj}$ be jth subtree of tree $T_s$.

Let $\{S_{gl}\}$ stand for an unordered set of species represented in $S_{gi}$ such that each species is represented exactly once, and let $|\{S_{gl}\}|$ and $\{|S_{gl}|\}$ be the number of entries in $\{S_{gl}\}$ and the number of pending vertices in $S_{gl}$, respectively. Define by $S_{sj}(S_{gl})$ the unique subtree of $S_{sj}$ that has leaves labeled exclusively with species from $|\{S_{gl}\}|$, so that each element of $|\{S_{gl}\}|$ is used i.e., that is, the unique subtree obtained by eliminating from $S_{sj}$ all species that are not present in $|\{S_{gl}\}|$.

Then define similarity measure, $\sigma$, between $S_{gi}$ and $S_{sj}$ in the following way:

$$\sigma(S_{gi},S_{sj})=0 \text{ if } |S_{gl}| \neq |\{S_{gl}\}|, \text{ or } S_{sj}(S_{gl}) \neq S_{gl}, \text{ and } \sigma(S_{gi},S_{gl})=|S_{gl}|$$

The support of tree clusters by data can be measured using the bootstrap technique described in Felsenstein (1985, Evolution 39:783–791).

In an embodiment of the invention, the human antiquitin gene was identified using phylogenetic analysis. The aldehyde dehydrogenase gene family in humans can be subdivided into at least ten ancient subtrees characterized by different functions of corresponding proteins. These genes probably arose from a series of gene duplications of an ancestral gene which took place before the divergence of a common ancestor of Eukaryotes and Eubacteria.

The aldehyde dehydrogenase gene cluster is highlighted in FIG. 5 which shows the original tree of ALDH sequences, the circled area indicating a sequence cluster where bacterial (*Bacillus subtilis*), plant (*Brassica napus*), and nematode (*Caenorhabditis elegans*) ortholog is present, but a human ortholog is not known. A random screening of cDNA libraries showed that a human ortholog, referred to as antiquitin, does exist. FIG. 6 shows the same gene tree as in FIG. 5 with an additional human protein referred to as antiquitin present in the tree.

In yet another embodiment of the invention, a human ortholog of the murine Max-interacting transcriptional repressor Mad3 was identified through phylogenetic analysis of a gene family. The gene tree was constructed as follows. The protein sequences of known members of the Mad gene family were extracted from GenBank database. The extracted sequences were aligned using multiple alignment program CLUSTALW running on Sun SPARC station. Redundant and non-homologous sequences as well as distant homologs from *S. cerevisiae, C. elegans, D. melanogaster* etc. were removed from the alignment. The refined set of sequences were realigned with CLUSTALW and a gene tree as presented in FIG. 17A was computed. To identify a human ortholog of the Mad3 protein, a human dbEST at NCBI was searched with program TBLASTN using mouse Mad3 protein sequences as a query. Two highly homologous ESTs were identified and are presented in FIG. 16A. To obtain a complete coding sequence a search was conducted to obtain overlapping sequences in dbEST. The search for overlapping sequences was performed using the program Iterate with EST Zs77e55.rl (gb/AA278224) as the search query. The search identified a single overlapping sequence. The search for overlapping sequences was performed using program Iterate with EST zs77e55.rl (gb/AA278224) serving as a query. The search returned a single overlapping sequence, namely HUMGS0012279 (dbj/C02407), thus showing that the two EST sequences found during the initial TBLASTIN search belong to the same gene. The complete sequence of the gene was assembled from the two ESTs using commercially available sequence assembly program SeqMan11(DNASTAR Inc., WI). The nucleotide sequence of the human Mad3 gene is presented in FIG. 16B. The deduced amino acid sequence of which is presented in FIG. 16C. The complete DNA sequence is also shown.

The present invention relates to nucleic acid molecules encoding the human Mad3 protein shown in FIG. 16C. The invention also relates to nucleic acid molecules that hybridize to the nucleic acid molecule of FIG. 16B under conditions of high stringency and encode a Mad3 protein. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH7.5), ImM EDTA, 0.02% PVP, 0.02% Ficoll, 0.02% BSA and 500 mg/ml denatured salmon sperm DNA. Filters are hybridized for 48 hours at 65° C. in prehybridization mixture containing 100 mg/ml denatured salmon sperm DNA and 5–20×10$^6$ CpM of $^{32}$P-labeled probe. Washing of filters is done at 37° C. for 1 hour in a solution containing 2×SSC, 0.01% PVP, 0.01% Ficoll and 0.01% BSA. This is followed by a wash in 0.1×SSC at 50° C. for 45 minutes before autoradiography. Other conditions of high stringency which may be used are well known in the art.

5.3. Simulation and Hypothesis Testing

The simulation and hypothesis testing methods of the invention, described in the subsections below, utilize specialized databases of gene/protein structures and interactions for identifying potentially undiscovered members of multi-gene families through comparisons of regulatory networks for different species, searching expressed sequence tag (EST) databases, and simulation of regulatory cascades.

5.3.1. Gene Discovery Through Analysis of Regulatory Networks

The present invention provides a method for identifying undiscovered genes through comparisons of regulatory networks for different species where functionally similar regulatory systems are conserved. The amount of information available concerning regulatory genes and/or proteins in different organisms and their functional relationships allows one to reconstruct and compare regulatory networks. Since in most cases, the knowledge of all genes involved in almost any particular regulatory system is incomplete, a comparison of homologous networks within the same organism and between different species permits the identification of genes absent in a system under comparison.

The identified genes, being part of a regulatory network, are implicated as potentially contributing to a phenotype of a disease associated with the system under analysis. Using the methods of the present invention these putative disease genes can be cloned, mapped and analyzed for mutations directly, thereby omitting the expensive and time-consuming steps of positional cloning and sequencing of genomic regions.

Gene discovery by analysis of regulatory networks is outlined in FIG. 7. The analysis is initiated starting with a biological system (e.g., signaling pathway of genes involved in Bcl-2-regulated apoptosis in lymphocytes), a single gene (e.g., Bcl-2) or a gene family (e.g., caspases).

Initially, a specialized database is generated for comparison of regulatory networks between different species. For example, starting with a single candidate gene in a single species, a typical iteration in this process begins with identification of all known proteins and genes that are upstream and downstream with respect to it in regulatory hierarchies and the reconstruction of a network of interacting genes and proteins. Next, for each protein, a set of key domains and motifs is identified and this information is used to search for related proteins in humans and other species. The identified sequences are compared and for each pair of sequences showing similarity above a certain threshold, a similarity object is generated. A similarity object is generated if two sequences, nucleotide or amino acid, show significant similarity in database searches (p value <0.001). The object retains the following information: (i) reference to similar substances i.e., genes or proteins; (ii) significance of the similarity, similarity score and percent of identity; and (iii) coordinates of the similarity region within two compared sequences.

"Orthology objects" constitute a subset of "similarity objects" which satisfies one additional requirement, i.e., that two similar sequences should be identified as orthologs by the tree-based algorithm described above. In identifying orthologs, if gene A is orthologous to gene B, and gene B is orthologous to gene C, gene A is necessarily orthologous to gene C.

In a specific embodiment of the invention, for each species under analysis, orthologous proteins or genes are identified. In a further embodiment of the invention, small orthologous molecules participating in a regulatory network for two or more species may also be identified. Where proteins, genes, or molecules are orthologs, the action of the protein, gene or molecule between species may be interchangeable. If more than two species are involved in the analysis, subtrees of orthologous substances and subtrees of orthologous actions are identified.

Once orthologous genes, proteins or molecules are identified in two or more species, by forming a reconciled tree, for example, a set of orthologous or paralogous regulatory networks can be analyzed and visualized using graph theory where arcs represent actions and vertices represent substances. Thus, the method of the invention may further comprise the following steps: (i) superimposing the orthologous regulatory networks from two or more species and searching for the actions (arcs) and substances (vertices) in the homologous networks that are represented in some taxa but absent in others; (ii) superimposing paralogous regulatory networks from the same taxa and searching for paralogous genes that are missing in some taxa; and (iii) computing a general regulatory network that summarizes common regulatory sequence relationships known for more than one species.

In a specific embodiment of the invention a set of regulatory networks from different species, relating to the same biological system, apoptosis, for example, can be analyzed and visualized utilizing the following methods: (i) for each species functional information is collected relating to apoptosis; (ii) using the functional information, regulatory networks for each species comprised of interacting proteins and/or the genes involved in apoptosis are generated; (iii) the sequences of the interacting proteins and genes of each of the regulatory network are compared and for sequences showing similarity above a predetermined threshold range; and (iv) distinguishing between orthologs and paralogs using the methods set forth above.

An analysis similar to that performed using subtrees of sequences may be applied to classify protein functions as orthologous or paralogous actions. A "generalized" regulatory network maybe represented as a network wherein a substance as it occurs in a particular species is substituted with a cluster (i.e., subtree) of orthologous substances among species. In the final step of the analysis the clusters within each species are compared to one another, to identify missing genes.

FIG. 8 depicts the regulatory relationships among hypothetical proteins (denoted with Arabic numerals) of hypothetical species A and B. As indicated in FIG. 8A, an overlay of regulatory data for two species overlaps, but not completely. As indicated, protein 5 is known only for species B while protein 3 is known only for species A. The proteins in different species denoted with the same numeral are considered orthologous. As indicated, the regulatory relationships between a pair of proteins can be of three different kinds. FIGS. 8B, 8C, and 8D represent Boolean operations, OR, AND, and XOR, as arcs of the two regulatory relationships depicted in FIG. 8A, the same operations being applicable to the set of vertices of the two regulatory relationships.

In some instances, orthologous networks in two distantly related taxa may have the same domains but arrangement of the domains between the related taxa may be different. In such a case, a one-to-one correspondence between orthologous proteins in closely related species has to be substituted with a one-to-many relationship among domains comprised within the proteins. For this purpose, a similarity object may be defined operating on pairs of motifs/domains in two proteins, and substitute pairs of orthologous proteins with pairs of orthologous domains. After this correction, homologous networks are compared as described above.

FIG. 9 is a diagram representing a hypothetical example of defining homologous protein networks in two different species using protein motifs, the diagram showing only two hypothetical proteins (lane 2) for species A and three hypothetical proteins (lanes 1, 3, and 4) for species B. Protein 1 in both species has motifs α and β, protein 2 has motifs δ, ε, and ζ, and proteins 3 and 4 have motifs δ and ζ, and ε, respectively. The motif analysis indicates that proteins 3 and 4 in species B may collectively perform the same function as protein 2 in species A.

5.3.2 Gene Discovery Based on Protein Motif/Domain Searches

The present invention provides yet another method for identifying genes that are homologous and perform the same or an analogous function in different species. The method of the invention comprises the following steps: (i) creating a database of sequences which comprise a motif or domain composition of a gene of interest using, for example, HMMER software; and (ii) searching additional databases for expressed sequence tags (ESTs) containing the domains and motifs characteristic for the gene of interest with HMMs of domains and motifs identified in step (i). In yet another embodiment of the invention, sequences may be searched which correspond to nucleotide sequences in an EST database or other cDNA databases using a program such as BLAST and retrieving the identified sequences. In an optional step, for each EST identified, sequence databases can be searched for overlapping sequences for the purpose of assembling longer overlapping stretches of DNA. Once identified, the ESTs can be used to isolate full length nucleotide sequences comprising the gene of interest using methods such as those described in Section 5.4, infra.

The general flowchart scheme for gene discovery analysis based on motif/domain search is shown in FIG. 10. In a specific embodiment of the invention, the method referred to as the "phylogenetic reflection technique" comprises, first, defining the motif or domain composition of a gene of interest involved in a biological system of interest. Second, protein-coding genes from other species, including for example yeast and/or nematode genes, that bear a significant similarity to the gene of interest or a specified domain of the corresponding protein are collected. Third, the identified genes are in turn subjected to a "domain analysis" to establish protein motifs which might suggest a function of these genes using, for example, HMMER software. Fourth, the selected genes are in turn used for database searches in EST databases (dbEST) and/or a non-redundant (nr) database to identify unknown genes that are potentially orthologous to the selected yeast and nematode genes. Once identified ESTs having different tumor suppressor domains may be linked using multiple PCR primers. Using routine cloning techniques, well known to those of skill in the art, a full length cDNA representing the gene of interest can be obtained.

Once new genes are identified by domain/motif analysis experimental searches may be carried out to isolate complete coding sequences and evaluate their tissue- and disease-specific expression patterns. In parallel their position with respect to regulatory networks can be identified as described below.

In a specific embodiment of the invention, an apoptosis related human gene was identified using the method described above. As a first step C. elegans genes containing either POZ or Kelch domains were identified. A Hidden Markov Model was developed using POZ and Kelch sequences from the Drosophila Kelch protein and any identified homologs. The resulting Hidden Marker Model was used to search through the collection of C. elegans protein sequences. One of the identified C. elegans genes contained a POZ domain, death domain, kinase domain and heat repeat. The presence of both a death domain and a kinase domain suggested that the protein functions as a regulatory protein.

A human EST database was searched using the protein sequence of the identified C. elegans gene and two sequences were identified (FIG. 13A). A gene tree was computed to determine whether the identified human sequences were orthologs of the C. elegans gene. As depicted in FIG. 13B, the human EST AA481214 appears to be a true ortholog of the C. elegans gene. FIG. 13C presents the nucleotide sequence of the identified death domain gene. FIG. 13D presents the amino acid sequence of the death domain protein.

The present invention encompasses the nucleic acid molecule of FIG. 13C, comprising the sequence of EST AA481214 and proteins encoded by said nucleic acid molecule. The invention also relates to nucleic acid molecules capable of hybridizing to such a nucleic acid molecule under conditions of high stringency. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH7.5), lmM EDTA, 0.02% PVP, 0.02% Ficoll, 0.02% BSA, and 500 mg/ml denatured salmon sperm DNA. Filters are hybridized for 48 hours at 65° C. in prehybridization mixture containing 100 mg/ml denatured salmon sperm DNA and 5–20×10$^6$ CpM of $^{32}$P-labeled probe. Washing of filters is done at 37° C. for 1 hour in a solution containing 2×SSC, 0.01% PVP, 0.01% Ficoll and 0.01% BSA. This is followed by a wash in 0.1×SSC at 50° C. for 45 minutes before autoradiography. Other conditions of high stringency which may be used are well known in the art.

5.3.3. Simulation of Regulatory Cascades

In an embodiment of the invention, an interactive graphical program is utilized for visualizing the scheme of regulatory relationships, "current" states of the substances, and active and inactive actions between pairs of substances. Such a program can be utilized for identification of genes which are associated with a specific disease. Currently, disease associated genes are discovered through positional cloning methods which combine methods of genetics and physical mapping with mutational analysis. The present invention provides a novel method for discovering disease associated genes.

For simulating regulatory cascades, it is assumed that the time in a simulated regulatory system advances in discrete "quanta," or periods of time. The "state of substances" of the system for each discrete period of time is computed by: creating a set of substance objects, where a set of interactions between each created substance object is known, an initial state is specified. The time is initially set to zero. All defined actions are observed to confirm that the substances corresponding to the actions (i) exist, and (ii) are in the right initial states. Action is defined by a pair of substances that are in suitable states. The "subject" substance is in the inactive state, while the "object" substance can be in either active, or inactive, state depending on the action type. For example, the action "dephosphorylation" requires an active phosphatase ("subject" substance) and a phosphorylated substitute protein ("object" substance) in phosphorylated form. If both conditions are satisfied, the action is recorded as in progress. At termination, the substances must change their states as specified by the action. On each following "quantum" of time, the simulation proceeds in the same way while maintaining the "bookkeeping" of the remaining time for each action and the remaining lifespan of each substance. The simulation stops when there are no more active actions available. The program allows editing of the properties of the objects, changing the scale and focus of the visualized simulation, and experimenting with the systems output.

In a specific embodiment of the invention a "knock out" of a gene can be simulated to model the regulatory system that normally includes hypothetical gene A. One of the typical questions related to the gene knock out is how does the knock out affect a biological pathway of interest. A hypothetical example of evaluating the impact of a knock out of hypothetical gene A on the expression of a hypothetical gene B is shown in FIG. 11. The answer to such a question could be "gene B will be inhibited" or "gene B will be induced" or "no effect".

In the practice of the present invention, a simple algorithm involving multiplication of gene interaction "signs" along the shortest pathway between the genes can be used to determine the outcome. The algorithm involves the following steps: (i) identification of the shortest non-oriented pathway connecting genes A and B involved in a pathway of interest; (ii) assigning sign "−" to gene A since it is knocked out and taking this sign as the initial sign value; (iii) moving along the shortest pathway between genes A and B, multiplying the current value of the sign with the sign of the next arc, where "−" stands for inhibition, "+" stands for induction or activation, and "0" stands for the lack of interaction between two proteins in the specified direction; (iv) determining if the final result of multiplication is "0", if so eliminating the zero arc and trying to find the shortest oriented bypass pathway between A and B in the remaining network; otherwise stop.

The final value of the sign at the moment of arriving at vertex B would indicate the most likely effect of the knock out of gene A which can be any one of the following: inhibition of gene B, induction/activation of gene B, or none. In addition to the "electronic knock out", an "electronic knock in" of a particular gene can be simulated. In such a computer simulation, the artificial addition of a gene and its effect on a regulatory system may be analyzed.

5.4. Identification and Isolation of Novel Genes

The present invention relates to identification of novel genes, i.e., missing orthologs or paralogs, and the isolation of nucleic acid molecules encoding novel genes. In a specific embodiment, a nucleic acid molecule encoding a missing ortholog or paralog can be isolated using procedures well known to those skilled in the art (See, for example, Sambrook et al., 1989, Molecular Cloning, A Laboratory Manual, 2d Ed., Cold Spring Harbor Laboratory Press, Cold Spring Harbor, N.Y. Glover, D. M. (ed.), 1985, DNA Cloning: A Practical Approach MRL Press, Ltd., Oxford, U.K. Vol. I, II.).

For example, genomic and/or cDNA libraries may be screened with labeled DNA fragments derived from a known ortholog or paralog from a specific species and hybridized to the genomic or cDNA libraries generated from a different species. For cross species hybridization, low stringency conditions are preferred. For same species hybridization, moderately stringent conditions are preferred. Any eukaryotic cell potentially can serve as the nucleic acid source for the molecular cloning of the gene of interest. The DNA may be obtained by standard procedures known in the art from cloned DNA (e.g., a DNA "library"), by cDNA cloning, or by the cloning of genomic DNA, or fragments thereof, purified from the desired cell.

By way of example and not limitation, procedures using conditions of low stringency are as follows (see also Shilo and Weinberg, 1981, Proc. Natl. Acad. Sci. USA 78:6789–6792; and Sambrook et al. 1989, Molecular Cloning, A Laboratory Manual, 2d Ed., Cold Spring Harbor Laboratory Press, Cold Spring harbor, N.Y.): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 mg/ml denatured salmon sperm DNA. Hybridizations are carried out in the same solution with the following modifications: 0.02% PVP, 0.02% Ficoll, 0.2% BSA, 100 mg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross species hybridizations).

In another specific embodiment, a nucleic acid which is hybridizable to a nucleic acid under conditions of moderate stringency is provided. For example, but not by way of limitation, procedures using such conditions of moderate stringency are as follows: filters containing DNA are pretreated for 6 h at 55° C. in a solution containing 6×SSC, 5× Denhart's solution, 0.5% SDS and 100 mg/ml denatured salmon sperm DNA. Hybridizations are carried out in the same solution and 5–20×10$^6$ CpM $^{32}$P-labeled probe is used. Filters are incubated in the hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

For expression cloning (a technique commonly used in the art), an expression library is constructed. For example, mRNA is isolated from the cell type of interest, cDNA is made and ligated into an expression vector (e.g., a bacteriophage derivative) such that it is capable of being expressed by a host cell (e.g., a bacterium) into which it is then introduced. Various screening assays can then be used to select for the expressed gene product of interest based on the physical, chemical, or immunological properties of its expressed product. Such properties can be deduced from the properties of the corresponding orthologs from other species.

In another embodiment, polymerase chain reaction (PCR) can be used to amplify the desired sequence from a genomic or cDNA library. To isolate orthologous or paralogous genes from other species, one synthesizes several different degenerate primers, for use in PCR reactions. In a preferred aspect, the oligonucleotide primers represent at least part of the gene comprising known ortholog or paralog sequences of different species. It is also possible to vary the stringency of hybridization conditions used in priming the PCR reactions, to allow for greater or lesser degrees of nucleotide sequence similarity between the known nucleotide sequences and the nucleic acid homolog being isolated.

Synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and a thermostable polymerase, e.g., Amplitaq (Perkin-Elmer). The nucleic acids being amplified can include mRNA or cDNA or genomic DNA from any eukaryotic species. After successful amplification of a segment of a the gene of interest, that segment may be molecularly cloned and sequenced, and utilized as a probe to isolate a complete cDNA or genomic clone.

Once identified and isolated the gene of interest can then be inserted into an appropriate cloning vector for amplification and/or expression in a host. A large number of vector-host systems known in the art may be used. Possible vectors include, but are not limited to, plasmids and modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini.

6. Example: Use of Specialized Databases For Identification of Novel Genes

To test the method of using databases for gene discovery, protein sequence and domain/motif databases specific to two overlapping functional groupings of proteins: (i) proteins known to be tumor suppressors, and (ii) proteins implicated in apoptosis in animals were developed.

6.1 Apoptosis Gene Discovery Method

Identification of a putative apoptosis-related human gene began with an identification of all genes in *C. elegans* that contained either a POZ or kelch domain. A subset of these genes is shown in FIG. 12. Hidden Markov Models (HMM) for the POZ and Kelch domains were built as follows. Starting with POZ and kelch sequences from the Drosophilia kelch protein (gi|577275) homologs were identified in other protein sequences using the BLASTP program. The resulting sequences showing significant similarity (e-value less than 0.001) were aligned using CLUSTALW program and the alignments were used to build Hidden Markov Models with HMMER-2 package. A computer printout listing of HMM models of tumor suppressors appears as a Microfiche Appendix to the present specification.

The resulting models were used to search through a database collection of *C. elegans* protein sequences. The domain structures of proteins having either a POZ or kelch domain were identified using existing collections of protein domains.

One of the unannotated protein-coding genes of *C. elegans* (corresponding protein accession number gi|1132541, see FIG. 12) appeared to include a POZ domain, death domain, kinase domain, and heat repeat. A death domain is characteristic for the apoptosis system and a kinase domain indicates that the protein is likely to participate in phosphorylation of other proteins. The presence of these particular domains suggests that this protein is serving as a regulatory protein.

Using the protein sequence of gi|1132541, the database of human EST sequences was searched and a number of partial human cDNA sequences representing potential human orthologs or paralogs of the *C. elegans* gi|1132541 were identified.

The two closest human sequences, AA481214 and W51957, are depicted in FIG. 13A. To determine whether the identified human sequences were orthologs or paralogs to the gi|1132541 gene of *C. elegans*, a gene tree (Saito and Nei, 1997, Molecular Biol. Evol. 4:406–425) was computed. The gene tree was generated using homologous genes identified with a BLASTP search against NCBI non-redundant database, using the human EST AA481214 sequence as a query. The resulting tree indicates that the identified human EST AA481214 represents a true ortholog of the *C. elegans* gene gi|1132541 (FIG. 13B). The nucleotide sequence of the death domain protein is shown in FIG. 13C, as well as the deduced amino acid sequence presented in FIG. 13D.

6.1.2 Apoptosis Gene Discovery Method

As a first step in identifying a novel gene involved in apoptosis, a comprehensive set of articles describing the system of apoptosis/programmed cell death in different species was compiled using the keyword "apoptosis". By analyzing the articles, information on regulatory pathways characterizing this system in different species, i.e., *C. elegans*, mouse, fruit fly, chicken, and human, was extracted. The regulatory information was stored as a collection of schemes produced in PowerPoint (Microsoft). FIG. 3 shows a set of keywords defining proteins involved in apoptosis pathways. The keywords were used to generate a specialized sequence database, referred to as Apoptosis3, utilizing the PsiRetriever program for extraction of proteins from the all-inclusive non-redundant GenBank database (NCBI). Using program PsiRetriever, sequences from the non-redundant (NCBI) database of protein sequences, were retrieved and stored as a FASTA file. The FASTA file was then converted into binary blast database using program FORMATDB from the BLAST suit of programs.

Genomic and cDNA sequences located in the region of human chromosome 13q were compared with the Apoptosis3 database using BLASTALL program from BLAST program complex. This region of the human genome is associated with Chronic Lymphocytic Leukemia (CLL). The comparison revealed significant similarity between a CLL region open reading frame and the mouse RPT1 protein (sp|P15533|RPT1) (FIG. 14). Analysis of regulatory functions of RPT1 in the mouse reveals that this gene functions as a repressor of the interleukin 2 receptor (IL-2R) gene. When the RPT1 gene is knocked out, the regulatory effect is manifested as a block of the apoptotic pathway in T lymphocytes resulting in an accumulation of T lymphocytes in blood. This result is consistent with aberrations observed in CLL, namely abnormal accumulation of B-cells in the blood (Trentin L. et al., 1997, Leuk. Lymphoma 27:35–42) and mutations in the human RPT1 gene play a role in development of CLL.

6.1.3 Example: A Discovery of A Human Ortholog of the Murine Max-Interacting Transcriptional Repressor The family of Myc proto-oncogenes encodes a set of transcription factors implicated in regulation of cell proliferation, differentiation, transformation and apoptosis. C-Myc null mutations result in retarded growth and development of mouse embryos and are lethal by 9–10 day of gestation. In contrast, overexpression of Myc genes inhibits cell differentiation and leads to neoplastic transformation. Moreover, deregulation of Myc expression by retroviral transduction, chromosomal translocation or gene amplification is linked to a broad range of naturally occurring tumors in humans and other species.

Another protein, called Max, is an obligatory heterodimeric partner for Myc proteins in mediating their function as activators of transcription during cell cycle progression, neoplastic transformation and programmed cell death (apoptosis). In order to make an active transcription factor the Myc proteins must form heterodimers with Max protein. This interaction with Max protein is necessary for specific binding of Myc with CACGTG box (or related E-boxes) on DNA and for activation of promoters located proximal to the binding sites.

Besides the Myc family of transcription factors, the Max protein forms complexes with another family of so-called MAD proteins: Mxi1, MAD1, MAD3 and MAD4. Whereas Myc:Max complexes activate transcription, MAD:Max complexes work in an opposite way repressing the transcription through the same E-box binding sites and apparently antagonize Myc-mediated activation of the same set of target genes.

During tissue development a shift from Myc:Max to MAD:Max complexes occurs coincidentally with the switch from cell proliferation to differentiation. The switch in heterocomplexes is thought to reflect a switch from activation to repression of common genes leading to cessation of proliferation, exiting the cell cycle and the beginning of cell differentiation. In differentiating neurons, primary keratinocytes, myeloid cell lines and probably other tissues the expression of different MAD:Max complexes appear in sequential order during the transition from cell proliferation to differentiation. The MAD3 expression appears first and it is restricted to proliferating cells prior to differentiation where it is co-expressed with two different member of Myc family, c-Myc or N-Myc. Mxi1 transcripts are detected in proliferating and differentiating cells whereas MAD1 and MAD4 were confined to post-mitotic cells. Because Myc expression is not always downregulated in post-mitotic cells, co-expression of Myc and MAD genes may result in competition for Max heterodimers thus providing promoting or inhibitory effect on cell proliferation.

The gene expression patterns, along with ability of Mad proteins to suppress Myc-dependent transformation, are consistent with a potential function of Mad genes as tumor suppressors. This view is supported by the fact that allelic loss and mutations were detected at the Mxi1 locus in prostate cancers (Eagle et al., 1995 Nat Genet 9:249–55). Cloning of the murine proteins Mad3 and Mad4 as well as their relation to Max signaling network was described by Hurlin (Hurlin P J, et al., 1995, EMBO J. 14:5646–59) and Queva (Queva et al. 1998 Oncogene 16:967–977). Human orthologs of Mad4, Mad1 and Mxi1 are known.

In this example, the discovery of an unknown human ortholog of Mad3 protein found "in silico," by means of phylogenetic analysis of known mouse and human members of the Mad gene family and database searches is described. Since the function of murine Mad3 as a Max-interacting transcriptional repressor of Myc-induced neoplastic transformation is well described, we can assign the same function to its human ortholog.

The gene tree shown in the FIG. 17 was constructed in the following way. The protein sequences of known members of Mad gene family were extracted from GenBank database using NCBI Entrez keyword searches. The extracted sequences were aligned using multiple alignment program Clustalw running on Sun SPARC station. The quality of the multiple alignment was checked using program HitViewer Iterate (A. Rzhetsky, available upon request) and the redundant, non-homologous sequences as well as distant homologs from S. cerevisiae, C. elegans, D. melanogaster etc. were removed from the alignment. The refined set of sequences was realigned with Clustalw and a gene tree as presented in FIG. 16A was computed from the alignment using program NJBOOT running on Sun SPARC station and viewed with program TreeView.

The tree presented in FIG. 17A clearly shows the relationships between three known mouse genes and their two human homologs. Attempts to find a missing human ortholog of the mouse Mad3 gene in protein non-redundant database at NCBI using BLAST search did not identify any human homologs other than sequences that were already present on the tree, confirming the absence of a known human ortholog for Mad3 protein in the database.

In order to identify a human ortholog of the Mad3 protein, a human dbEST at NCBI was searched with program TBLASTN using Mad3 protein sequence as a query. Two EST were identified and are shown in FIG. 16A.

Due to the nature of dbEST database this search produced only partial sequences of potential candidate genes. To obtain complete coding sequences (complete cds) of the genes, a search was conducted to obtain overlapping sequences in dbEST. The search for overlapping sequences was performed using the program Iterate with EST zs77e55.r1 (gb|AA278224) serving as a query. The search returned a single overlapping sequence, namely HUMGS0012279 (dbj|C02407), thus indicating that the two EST sequences found during the initial TBLASTN search belong to the same gene.

The complete sequence of the gene was assembled from the two ESTs using commercially available sequence assembly program SeqManII (DNASTAR Inc., WI). The nucleotide sequence of the human Mad3 gene is presented in FIG. 16B. The deduced amino acid sequence of the gene is presented in FIG. 16C. The translated sequence consists of 206 amino acid residues 81% of which are identical to mouse Mad3 protein. The alignment of human and mouse Mad3 proteins shown below was made using BLAST server at NCBI and is presented in FIG. 16C.

Multiple alignment of the new sequence with sequences of known Mad proteins was made using Clustalw and viewed with the HitViewer. A gene tree was computed from this alignment using NJBOOT. Multiple alignment of the new sequence with sequences of known Mad proteins (FIG. 16C) along with its position on gene tree (FIG. 17B) shows that this new human gene found by the approach described above belongs to the family of Mad proteins and is the ortholog of mouse Mad3.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. A method for identifying the affect of a gene knockout on a regulatory pathway comprising the following steps:
   (i) identification of the shortest regulatory pathway connecting two gene products;
   (ii) assigning an initial sign value of "−" to the knockout gene product;
   (iii) multiplying the initial sign value of the knockout gene product with the sign value of the adjacent gene product in the pathway, wherein "−" stands for inhibition. "+" stands for induction or activation, and "0" stands for the lack of interaction between two gene products; and
   (iv) determining the final sign value at the end of the pathway, wherein "−" indicates inhibition and "+" indicates induction or activation of the pathway.

2. A method for identifying a novel nucleic acid molecule encoding a protein of interest comprising:
   (i) selecting a gene of interest and searching a database for homologous sequences derived from one or more species;
   (ii) aligning the homologous sequences identified in step (i) with the gene of interest to form a sequence alignment;
   (iii) constructing a gene tree using the sequence alignment;
   (iv) constructing a species tree;
   (v) imputing the species tree and gene tree into an algorithm which integrates the species tree and the gene free into a reconciled tree wherein the following algorithm is used to integrate the species tree and the gene tree into a reconciled tree:
      (a) computing the similarity $\sigma(S_{gi}, S_{sj})$ for each pair of interior nodes from trees $T_g$ and $T_s$,
      (b) finding the maximum $\sigma(S_{gi}, S_{sj})$;
      (c) saving $S_{gi}$ as a new cluster of orthologs, save $\{S_{gi}\}=\{S_{sj}\}$ as a set of species that are likely to have gene of this kind (or lost it in evolution);
      (d) eliminating $S_{gi}$ from $T_g$; $T_g:=T_g\backslash S_{gi}$:
      (e) repeating step (ii)–(iv) until $T_g$ is non-empty;
   (vi) identifying orthologous gene products present in one species but missing in another; and
   (vii) isolating a nucleic acid molecule encoding the gene products identified in step (vi) from a nucleic acid sample derived from the species in which the gene product is absent.

* * * * *

UNITED STATES PATENT AND TRADEMARK OFFICE
CERTIFICATE OF CORRECTION

| | |
|---|---|
| PATENT NO. | : 6,633,819 B2 |
| APPLICATION NO. | : 09/327983 |
| DATED | : October 14, 2003 |
| INVENTOR(S) | : Rzhetsky et al. |

It is certified that error appears in the above-identified patent and that said Letters Patent is hereby corrected as shown below:

IN THE SPECIFICATION:
On Page 1, Column 1, line 9, please insert the following header and paragraph:

-- Statement Regarding Federally Sponsored Research or Development
This invention was made with government support under grant numbers LM006274 and LM005627 awarded by the National Institutes of Health. The government has certain rights in the invention. --

Signed and Sealed this

First Day of July, 2008

JON W. DUDAS
*Director of the United States Patent and Trademark Office*

SEQUENCE LISTING

<160> NUMBER OF SEQ ID NOS: 18

<210> SEQ ID NO 1
<211> LENGTH: 405
<212> TYPE: DNA
<213> ORGANISM: Homo sapiens

<400> SEQUENCE: 1

| | | | | | | |
|---|---|---|---|---|---|---|
| catggcttcc | tggacaccaa | ccctgccatc | cgggagcaga | cggtcaagtc | catgctgctc | 60 |
| ctggccccaa | agctgaacga | ggccaacctc | aatgtggagc | tgatgaagca | ctttgcacgg | 120 |
| ctacaggcca | aggatgaaca | gggcccatc | cgctgcaaca | ccacagtctg | cctgggcaaa | 180 |
| atcggctcct | acctcagtgc | tagcaccaga | cacagggtcc | ttacctctgc | cttcagccga | 240 |
| gccactaggg | acccgtttgc | accgtcccgg | gttgcgggtg | tcctgggctt | tgctgccacc | 300 |
| cacaacctct | actcaatgaa | cgactgtgcc | agaagatcc | tgcctgtgct | ctgcggtctc | 360 |
| actgtagatc | ctgagaaatc | cgtgcgagac | caggccttca | aggca | | 405 |

<210> SEQ ID NO 2
<211> LENGTH: 453
<212> TYPE: DNA
<213> ORGANISM: Homo sapiens
<220> FEATURE:
<221> NAME/KEY: unsure
<222> LOCATION: (146)...(146)
<223> OTHER INFORMATION: A, C, G, or T

<400> SEQUENCE: 2

| | | | | | | |
|---|---|---|---|---|---|---|
| ccttcgagtt | cggcaatgct | ggggccgttg | tcctcacgcc | cctcttcaag | gtgggcaagt | 60 |
| tcctgagcgc | tgaggagtat | cagcagaaga | tcatccctgt | ggtggtcaag | atgttctcat | 120 |
| ccactgaccg | ggccatgcgc | atccgnctcc | tgcagcagat | ggagcagttc | atccagtacc | 180 |
| ttgacgagcc | aacagtcaac | acccagatct | cccccacgt | cgtacatggc | ttcctggaca | 240 |
| ccaaccctgc | catccgggag | cagacggtca | agtccatgc | gctcctggcc | caaagctga | 300 |
| acgaggccaa | cctcaatgtg | gagctgatga | agcactttgc | acggctacag | gccaaggatg | 360 |
| aacagggccc | catccgctgc | aacaccacag | tctgcctggg | caaaatcggc | tcctacctca | 420 |
| gtgctagcac | cagacacagg | gtccttacct | ctg | | | 453 |

<210> SEQ ID NO 3
<211> LENGTH: 1727
<212> TYPE: DNA
<213> ORGANISM: Homo sapiens

<400> SEQUENCE: 3

| | | | | | | |
|---|---|---|---|---|---|---|
| cagccgaagc | amgcaaaaat | tcttccagga | gctgagcaag | agcctggacg | cattccctga | 60 |
| ggayttctgt | cggcacaagg | tgctgcccca | gctgctgacc | gccttcgagt | tcggcaatgc | 120 |
| tggggccgtt | gtcctcacgc | ccctcttcaa | ggtgggcaag | ttcctgagcg | ctgaggagta | 180 |
| tcagcagaag | atcatccctg | tggtggtcaa | gatgttctca | tccactgacc | gggccatgcg | 240 |
| catccgcctc | ctgcagcaga | tggagcagtt | catccagtac | cttgacgagc | caacagtcaa | 300 |
| cacccagatc | ttcccccacg | tcgtacatgg | cttcctggac | accaaccctg | ccatccggga | 360 |
| gcagacggtc | aagtccatgc | tgctcctggc | cccaaagctg | aacgaggcca | acctcaatgt | 420 |
| ggagctgatg | aagcactttg | cacggctaca | ggccaaggat | gaacagggcc | ccatccgctg | 480 |
| caacaccaca | gtctgcctgg | gcaaaatcgg | ctcctacctc | agtgctagca | ccagacacag | 540 |

```
ggtccttacc tctgccttca gccgagccac tagggacccg tttgcaccgt cccgggttgc    600
gggtgtcctg ggctttgctg ccacccacaa cctctactca atgaacgact gtgcccagaa    660
gatcctgcct gtgctctgcg gtctcactgt agatcctgag aaatccgtgc agaccaggc    720 cttcaaggcm wttcggagct tcctgtccaa attggagtct gtgtcggagg acccgaccca    780
gctggaggaa gtggagaagg atgtccatgc agcctccagc cctggcatgg gaggagccgc    840
agctagctgg gcaggctggg cgtgaccggg gtctcctcac tcacctccaa gctgatccgt    900
tcgcacccaa ccactgcccc aacagaaacc aacattcccc aaagacccac gcctgaagga    960
gttcctgccc cagcccccac ccctgttcct gccaccccta caacctcagg ccactgggag   1020
acgcaggagg aggacaagga cacagcagag acagcagca ctgctgacag atgggacgac   1080
gaagactggg gcagcctgga gcaggaggcc gagtctgtgc tggcccagca ggacgactgg   1140
agcaccgggg gccaagtgag ccgtgctagt caggtcagca actccgacca caaatcctcc   1200
aaatccccag agtccgactg gagcagctgg gaarctgagg gctcctggga cagggctgg    1260 caggagccaa gctcccagga gccacctyct gacggtacac ggctggccag cgagtataac   1320
tggggtggcc cagagtccag cgacaagggc gaccccttcg ctaccctgtc tgcacgtccc   1380
agcacccagc cgaggccaga ctcttggggt gaggacaact gggagggcct cgagactgac   1440
agtcgacagg tcaaggctga gctggcccgg aagaagcgcg aggagcggcg gcgggagatg   1500
gaggccaaac gcgccgagag gaaggtgcca agggccccat gaagctggga gcccggaagc   1560
tggactgaac cgtggcggtg gcccttcccg gctgcggaga gcccgcccca cagatgtatt   1620
tattgtacaa accatgtgag cccggccgcc cagccaggcc atctcacgtg tacataatca   1680
gagccacaat aaattctatt tcacaaaaaa aaaaaaaaa aaaaaaa                  1727
```

<210> SEQ ID NO 4
<211> LENGTH: 287
<212> TYPE: PRT
<213> ORGANISM: Homo sapiens
<220> FEATURE:
<221> NAME/KEY: UNSURE
<222> LOCATION: (4)...(4)
<223> OTHER INFORMATION: Any amino acid
<220> FEATURE:
<221> NAME/KEY: UNSURE
<222> LOCATION: (244)...(244)
<223> OTHER INFORMATION: Any amino acid

<400> SEQUENCE: 4

```
Ser Arg Ser Xaa Gln Lys Phe Phe Gln Glu Leu Ser Lys Ser Leu Asp
 1               5                  10                  15

Ala Phe Pro Glu Asp Phe Cys Arg His Lys Val Leu Pro Gln Leu Leu
            20                  25                  30

Thr Ala Phe Glu Phe Gly Asn Ala Gly Ala Val Leu Thr Pro Leu
        35                  40                  45

Phe Lys Val Gly Lys Phe Leu Ser Ala Glu Glu Tyr Gln Gln Lys Ile
    50                  55                  60

Ile Pro Val Val Lys Met Phe Ser Ser Thr Asp Arg Ala Met Arg
65                  70                  75                  80

Ile Arg Leu Leu Gln Gln Met Glu Gln Phe Ile Gln Tyr Leu Asp Glu
                85                  90                  95

Pro Thr Val Asn Thr Gln Ile Phe Pro His Val His Gly Phe Leu
            100                 105                 110

Asp Thr Asn Pro Ala Ile Arg Glu Gln Thr Val Lys Ser Met Leu Leu
```

-continued

```
                115                 120                 125
Leu Ala Pro Lys Leu Asn Glu Ala Asn Leu Asn Val Glu Leu Met Lys
    130                 135                 140

His Phe Ala Arg Leu Gln Ala Lys Asp Glu Gln Gly Pro Ile Arg Cys
145                 150                 155                 160

Asn Thr Thr Val Cys Leu Gly Lys Ile Gly Ser Tyr Leu Ser Ala Ser
                165                 170                 175

Thr Arg His Arg Val Leu Thr Ser Ala Phe Ser Arg Ala Thr Arg Asp
                180                 185                 190

Pro Phe Ala Pro Ser Arg Val Ala Gly Val Leu Gly Phe Ala Ala Thr
                195                 200                 205

His Asn Leu Tyr Ser Met Asn Asp Cys Ala Gln Lys Ile Leu Pro Val
    210                 215                 220

Leu Cys Gly Leu Thr Val Asp Pro Glu Lys Ser Val Arg Asp Gln Ala
225                 230                 235                 240

Phe Lys Ala Xaa Arg Ser Phe Leu Ser Lys Leu Glu Ser Val Ser Glu
                245                 250                 255

Asp Pro Thr Gln Leu Glu Glu Val Glu Lys Asp Val His Ala Ala Ser
                260                 265                 270

Ser Pro Gly Met Gly Gly Ala Ala Ala Ser Trp Ala Gly Trp Ala
                275                 280                 285
```

<210> SEQ ID NO 5
<211> LENGTH: 223
<212> TYPE: PRT
<213> ORGANISM: Homo sapiens

<400> SEQUENCE: 5

```
Val Met Glu Leu Leu Glu Glu Asp Leu Thr Cys Pro Ile Cys Cys Ser
1               5                   10                  15

Leu Phe Asp Asp Pro Arg Val Leu Pro Cys Ser His Asn Phe Cys Lys
                20                  25                  30

Lys Cys Leu Glu Gly Ile Leu Glu Gly Ser Val Arg Asn Ser Met Trp
            35                  40                  45

Arg Pro Ala Pro Phe Lys Cys Pro Thr Cys Arg Lys Glu Thr Ser Ala
    50                  55                  60

Thr Gly Ile Asn Ser Leu Gln Val Asn Tyr Ser Leu Lys Gly Ile Val
65                  70                  75                  80

Glu Lys Tyr Asn Lys Ile Lys Ile Ser Pro Lys Met Pro Val Cys Lys
                85                  90                  95

Gly His Met Gly Gln Pro Leu Asn Ile Phe Cys Leu Thr Asp Met Gln
                100                 105                 110

Leu Ile Cys Gly Ile Cys Ala Thr Arg Gly Glu His Thr Lys His Val
            115                 120                 125

Phe Cys Ser Ile Glu Asp Ala Tyr Ala Gln Glu Arg Asp Ala Phe Glu
    130                 135                 140

Ser Leu Phe Gln Ser Phe Glu Thr Trp Arg Arg Gly Asp Ala Leu Ser
145                 150                 155                 160

Arg Leu Asp Thr Met Glu Thr Ser Lys Arg Lys Ser Leu Gln Leu Met
                165                 170                 175

Thr Lys Asp Ser Asp Lys Val Lys Glu Phe Phe Glu Lys Leu Gln His
                180                 185                 190

Thr Leu Asp Gln Lys Lys Asn Glu Ile Leu Ser Asp Phe Glu Thr Met
            195                 200                 205
```

Lys Leu Ala Val Met Gln Ala Tyr Asp Pro Glu Ile Asn Lys Leu
    210                 215                 220

<210> SEQ ID NO 6
<211> LENGTH: 218
<212> TYPE: PRT
<213> ORGANISM: Mouse

<400> SEQUENCE: 6

Val Leu Glu Met Ile Lys Glu Val Thr Cys Pro Ile Cys Leu Glu
 1               5                  10                  15

Leu Leu Lys Glu Pro Val Ser Ala Asp Cys Asn His Ser Phe Cys Arg
            20                  25                  30

Ala Cys Ile Thr Leu Asn Tyr Glu Ser Asn Arg Asn Thr Asp Gly Lys
        35                  40                  45

Gly Asn Cys Pro Val Cys Arg Val Pro Tyr Pro Phe Gly Asn Leu Arg
    50                  55                  60

Pro Asn Leu His Val Ala Asn Ile Val Glu Arg Leu Lys Gly Phe Lys
65                  70                  75                  80

Ser Ile Pro Glu Glu Gln Lys Val Asn Ile Cys Ala Gln His Gly
            85                  90                  95

Glu Lys Leu Arg Leu Phe Cys Arg Lys Asp Met Met Val Ile Cys Trp
            100                 105                 110

Leu Cys Glu Arg Ser Gln Glu His Arg Gly His Gln Thr Ala Leu Ile
        115                 120                 125

Glu Glu Val Asp Gln Glu Tyr Lys Glu Lys Leu Gln Gly Ala Leu Trp
    130                 135                 140

Lys Leu Met Lys Lys Ala Lys Ile Cys Asp Glu Trp Gln Asp Asp Leu
145                 150                 155                 160

Gln Leu Gln Arg Val Asp Trp Glu Asn Gln Ile Gln Ile Asn Val Glu
            165                 170                 175

Asn Val Gln Arg Gln Phe Lys Gly Leu Arg Asp Leu Leu Asp Ser Lys
            180                 185                 190

Glu Asn Glu Glu Leu Gln Lys Leu Lys Glu Lys Lys Glu Val Met
        195                 200                 205

Glu Lys Leu Glu Glu Ser Glu Asn Glu Leu
    210                 215

<210> SEQ ID NO 7
<211> LENGTH: 124
<212> TYPE: PRT
<213> ORGANISM: Mouse

<400> SEQUENCE: 7

Met Glu Pro Val Ala Ser Asn Ile Gln Val Leu Leu Gln Ala Glu
 1               5                  10                  15

Phe Leu Glu Arg Arg Glu Arg Glu Ala Glu His Gly Tyr Ala Ser Leu
            20                  25                  30

Cys Pro His His Ser Pro Gly Thr Val Cys Arg Arg Lys Pro Pro
        35                  40                  45

Leu Gln Ala Pro Gly Ala Leu Asn Ser Gly Arg Ser Val His Asn Glu
    50                  55                  60

Leu Glu Lys Arg Arg Arg Ala Gln Leu Lys Arg Cys Leu Glu Gln Leu
65                  70                  75                  80

Arg Gln Gln Met Pro Leu Gly Val Asp Cys Thr Arg Tyr Thr Thr Leu
            85                  90                  95

```
Ser Leu Leu Arg Ala Arg Val His Ile Gln Lys Leu Glu Glu Gln Glu
            100                 105                 110

Gln Gln Ala Arg Arg Leu Lys Glu Lys Leu Arg Ser
        115                 120
```

<210> SEQ ID NO 8
<211> LENGTH: 125
<212> TYPE: PRT
<213> ORGANISM: Homo sapiens

<400> SEQUENCE: 8

```
Met Glu Pro Leu Ala Ser Asn Ile Gln Val Leu Leu Gln Ala Ala Glu
 1               5                  10                  15

Phe Leu Glu Arg Arg Glu Arg Glu Ala Glu His Gly Tyr Ala Ser Leu
            20                  25                  30

Cys Pro His Arg Ser Pro Gly Pro Ile His Arg Arg Lys Lys Arg Pro
        35                  40                  45

Pro Gln Ala Pro Gly Ala Gln Asp Ser Gly Arg Ser Val His Asn Glu
    50                  55                  60

Leu Glu Lys Arg Arg Arg Ala Gln Leu Lys Arg Cys Leu Glu Arg Leu
65                  70                  75                  80

Lys Gln Gln Met Pro Leu Gly Gly Asp Cys Ala Arg Tyr Thr Thr Leu
                85                  90                  95

Ser Leu Leu Arg Arg Ala Arg Met His Ile Gln Lys Leu Glu Asp Gln
            100                 105                 110

Glu Gln Arg Ala Arg Gln Leu Lys Glu Arg Leu Arg Thr
        115                 120                 125
```

<210> SEQ ID NO 9
<211> LENGTH: 63
<212> TYPE: PRT
<213> ORGANISM: Mouse

<400> SEQUENCE: 9

```
Lys Gln Gln Ser Leu Gln Gln Leu Glu Leu Gln Gly Leu Pro
 1               5                  10                  15

Gly Ala Arg Glu Arg Glu Arg Leu Arg Ala Asp Ser Leu Asp Ser Ser
            20                  25                  30

Gly Leu Ser Ser Glu Arg Ser Asp Ser Asp Gln Glu Asp Leu Glu Val
        35                  40                  45

Asp Val Glu Asn Leu Val Phe Gly Thr Glu Thr Glu Leu Leu Gln
    50                  55                  60
```

<210> SEQ ID NO 10
<211> LENGTH: 63
<212> TYPE: PRT
<213> ORGANISM: Homo sapiens
<220> FEATURE:
<221> NAME/KEY: UNSURE
<222> LOCATION: (8)...(8)
<223> OTHER INFORMATION: Any amino acid

<400> SEQUENCE: 10

```
Lys Gln Gln Ser Leu Gln Arg Xaa Trp Met Gln Leu Arg Gly Leu Ala
 1               5                  10                  15

Gly Ala Ala Glu Arg Glu Arg Leu Arg Ala Asp Ser Leu Asp Ser Ser
            20                  25                  30

Gly Leu Ser Ser Glu Arg Ser Asp Ser Asp Gln Glu Glu Leu Glu Val
        35                  40                  45
```

```
Asp Val Glu Ser Leu Val Phe Gly Gly Glu Ala Glu Leu Leu Arg
    50                  55                  60
```

<210> SEQ ID NO 11
<211> LENGTH: 733
<212> TYPE: DNA
<213> ORGANISM: Homo sapiens
<220> FEATURE:
<221> NAME/KEY: unsure
<222> LOCATION: (481)...(481)
<223> OTHER INFORMATION: A, C, G, or T
<220> FEATURE:
<221> NAME/KEY: unsure
<222> LOCATION: (499)...(499)
<223> OTHER INFORMATION: A, C, G, or T
<220> FEATURE:
<221> NAME/KEY: unsure
<222> LOCATION: (690)...(690)
<223> OTHER INFORMATION: A, C, G, or T
<220> FEATURE:
<221> NAME/KEY: unsure
<222> LOCATION: (732)...(732)
<223> OTHER INFORMATION: A, C, G, or T

<400> SEQUENCE: 11

```
cagccgcttg ctccggccgg caccctaggc cgcagtccgc caggctgtcg ccgacatgga    60
acccttggcc agcaacatcc aggtcctgct gcaggcggcc gagttcctgg agcgccgtga   120
gagagaggcc gagcatggtt atgcgtccct gtgcccgcat cgcagtccag gccccatcca   180
caggaggaag aagcgacccc cccaggctcc tggcgcgcag acagcgggc ggtcagtgca    240
caatgaactg gagaagcgca ggagggccca gttgaagcgg tgcctggagc ggctgaagca   300
gcagatgccc ctgggcggcg actgtgcccg gtacaccacg ctgagcctgc tgcgccgtgc   360
caggatgcac atccagaagc tggaggatca ggagcagcgg gcccgacagc tcaaggagag   420
gctgcgcaca aagcagcaga gcctgcagcg gcantggatg cagctccggg ggctggcagg   480
ngcggccgag cgggagcgnc tgcgggcgga cagtctggac tcctcaggcc tctcctctga   540
gcgctcagac tcagaccaag aggagctgga ggtggatgtg gagagcctgg tgtttggggg   600
tgaggccgag ctgctgcggg gcttcgtcgc cggccaggag cacagctact cgcacgtcgg   660
cggcgcctgg ctatgatgtt cctcacccan ggcgggcctc tgccctctta ctcgttgccc   720
aagcccactt tnc                                                      733
```

<210> SEQ ID NO 12
<211> LENGTH: 227
<212> TYPE: PRT
<213> ORGANISM: Mouse

<400> SEQUENCE: 12

```
Met Ala Thr Ala Val Gly Met Asn Ile Gln Leu Leu Glu Ala Ala
 1               5                  10                  15

Asp Tyr Leu Glu Arg Arg Glu Arg Glu Ala Glu His Gly Tyr Ala Ser
                20                  25                  30

Met Leu Pro Tyr Ser Lys Asp Arg Asp Ala Phe Lys Arg Arg Asn Lys
            35                  40                  45

Pro Lys Lys Asn Ser Thr Ser Ser Arg Ser Thr His Asn Glu Met Glu
        50                  55                  60

Lys Asn Arg Arg Ala His Leu Arg Leu Cys Leu Glu Lys Leu Lys Gly
 65                  70                  75                  80

Leu Val Pro Leu Gly Pro Glu Ser Ser Arg His Thr Thr Leu Ser Leu
                85                  90                  95
```

```
Leu Thr Lys Ala Lys Leu His Ile Lys Lys Leu Glu Asp Cys Asp Arg
            100                 105                 110

Lys Ala Val His Gln Ile Asp Gln Leu Gln Arg Glu Gln Arg His Leu
            115                 120                 125

Lys Arg Arg Leu Glu Lys Leu Gly Ala Glu Arg Thr Arg Met Asp Ser
130                 135                 140

Val Gly Ser Val Val Ser Ser Glu Arg Ser Asp Ser Asp Arg Glu Glu
145                 150                 155                 160

Leu Asp Val Asp Val Asp Val Asp Val Asp Val Asp Val Glu Gly Thr
                    165                 170                 175

Asp Tyr Leu Asn Gly Asp Leu Gly Trp Ser Ser Val Ser Asp Ser
            180                 185                 190

Asp Glu Arg Gly Ser Met Gln Ser Leu Gly Ser Asp Glu Gly Tyr Ser
            195                 200                 205

Ser Ala Thr Val Lys Arg Ala Lys Leu Gln Asp Gly His Lys Ala Gly
            210                 215                 220

Leu Gly Leu
225

<210> SEQ ID NO 13
<211> LENGTH: 221
<212> TYPE: PRT
<213> ORGANISM: Homo sapiens

<400> SEQUENCE: 13

Met Ala Ala Ala Val Arg Met Asn Ile Gln Met Leu Leu Glu Ala Ala
1               5                   10                  15

Asp Tyr Leu Glu Arg Arg Glu Arg Glu Ala Glu His Gly Tyr Ala Ser
            20                  25                  30

Met Leu Pro Tyr Asn Asn Lys Asp Arg Asp Ala Leu Lys Arg Arg Asn
            35                  40                  45

Lys Ser Lys Lys Asn Asn Ser Ser Ser Arg Ser Thr His Asn Glu Met
50                  55                  60

Glu Lys Asn Arg Arg Ala His Leu Arg Leu Cys Leu Glu Lys Leu Lys
65                  70                  75                  80

Gly Leu Val Pro Leu Gly Pro Glu Ser Ser Arg His Thr Thr Leu Ser
                85                  90                  95

Leu Leu Thr Lys Ala Lys Leu His Ile Lys Lys Leu Glu Asp Cys Asp
            100                 105                 110

Arg Lys Ala Val His Gln Ile Asp Gln Leu Gln Arg Glu Gln Arg His
            115                 120                 125

Leu Lys Arg Gln Leu Glu Lys Leu Gly Ile Glu Arg Ile Arg Met Asp
130                 135                 140

Ser Ile Gly Ser Thr Val Ser Ser Glu Arg Ser Asp Ser Asp Arg Glu
145                 150                 155                 160

Glu Ile Asp Val Asp Val Glu Ser Thr Asp Tyr Leu Thr Gly Asp Leu
                    165                 170                 175

Asp Trp Ser Ser Ser Ser Val Ser Asp Ser Asp Glu Arg Gly Ser Met
            180                 185                 190

Gln Ser Leu Gly Ser Asp Glu Gly Tyr Ser Ser Thr Ser Ile Lys Arg
            195                 200                 205

Ile Lys Leu Gln Asp Ser His Lys Ala Cys Leu Gly Leu
            210                 215                 220

<210> SEQ ID NO 14
```

```
<211> LENGTH: 221
<212> TYPE: PRT
<213> ORGANISM: Homo sapiens

<400> SEQUENCE: 14

Met Ala Ala Val Arg Met Asn Ile Gln Met Leu Glu Ala Ala
1               5                   10                  15

Asp Tyr Leu Glu Arg Arg Glu Arg Glu Ala Glu His Gly Tyr Ala Ser
            20                  25                  30

Met Leu Pro Tyr Asn Asn Lys Asp Arg Asp Ala Leu Lys Arg Arg Asn
                35                  40                  45

Lys Ser Lys Asn Asn Ser Ser Arg Ser Thr His Asn Glu Met
50                  55                  60

Glu Lys Asn Arg Arg Ala His Leu Arg Leu Cys Leu Glu Lys Leu Lys
65                  70                  75                  80

Gly Leu Val Pro Leu Gly Pro Glu Ser Ser Arg His Thr Thr Leu Ser
                85                  90                  95

Leu Leu Thr Lys Ala Lys Leu His Ile Lys Lys Leu Glu Asp Cys Asp
            100                 105                 110

Arg Lys Ala Val His Gln Ile Asp Gln Leu Gln Arg Glu Gln Arg His
            115                 120                 125

Leu Lys Arg Gln Leu Glu Lys Leu Gly Ile Glu Arg Ile Arg Met Asp
        130                 135                 140

Ser Ile Gly Ser Thr Val Ser Ser Glu Arg Ser Asp Ser Asp Arg Glu
145                 150                 155                 160

Glu Ile Asp Val Asp Val Glu Ser Thr Asp Tyr Leu Thr Gly Asp Leu
                165                 170                 175

Asp Trp Ser Ser Ser Val Ser Asp Ser Asp Glu Arg Gly Ser Met
                180                 185                 190

Gln Ser Leu Gly Ser Asp Glu Gly Tyr Ser Ser Thr Ser Ile Lys Arg
            195                 200                 205

Ile Lys Leu Gln Asp Ser His Lys Ala Cys Leu Gly Leu
        210                 215                 220

<210> SEQ ID NO 15
<211> LENGTH: 207
<212> TYPE: PRT
<213> ORGANISM: Mouse

<400> SEQUENCE: 15

Met Glu Leu Asn Ser Leu Leu Leu Leu Glu Ala Ala Glu Tyr Leu
1               5                   10                  15

Glu Arg Arg Asp Arg Glu Ala Glu His Gly Tyr Ala Ser Met Leu Pro
            20                  25                  30

Phe Asp Gly Asp Phe Ala Arg Lys Lys Thr Lys Thr Ala Gly Leu Val
                35                  40                  45

Arg Lys Gly Pro Asn Asn Arg Ser Ser His Asn Glu Leu Glu Lys His
50                  55                  60

Arg Arg Ala Lys Leu Arg Leu Tyr Leu Glu Gln Leu Lys Gln Leu Gly
65                  70                  75                  80

Pro Leu Gly Pro Asp Ser Thr Arg His Thr Thr Leu Ser Leu Leu Lys
                85                  90                  95

Ala Lys Met His Ile Lys Lys Leu Glu Glu Gln Asp Arg Arg Ala Leu
            100                 105                 110

Ser Ile Lys Glu Gln Leu Gln Arg Glu His Arg Phe Leu Lys Arg Arg
        115                 120                 125
```

```
Leu Glu Gln Leu Ser Val Gln Ser Val Arg Val Arg Thr Asp Ser Thr
    130                 135                 140

Gly Ser Ala Val Ser Thr Asp Ser Glu Gln Glu Val Asp Ile Glu
145                 150                 155                 160

Gly Met Glu Phe Gly Pro Gly Glu Leu Asp Ser Ala Gly Ser Ser Ser
                165                 170                 175

Asp Ala Asp Asp His Tyr Ser Leu Gln Ser Ser Gly Cys Ser Asp Ser
                180                 185                 190

Ser Tyr Gly His Pro Cys Arg Arg Pro Gly Cys Pro Gly Leu Ser
                195                 200                 205
```

<210> SEQ ID NO 16
<211> LENGTH: 205
<212> TYPE: PRT
<213> ORGANISM: Mouse

<400> SEQUENCE: 16

```
Met Glu Pro Val Ala Ser Asn Ile Gln Val Leu Leu Gln Ala Ala Glu
1               5                   10                  15

Phe Leu Glu Arg Arg Glu Arg Glu Ala Glu His Gly Tyr Ala Ser Leu
                20                  25                  30

Cys Pro His His Ser Pro Gly Thr Val Cys Arg Arg Lys Pro Pro
            35                  40                  45

Leu Gln Ala Pro Gly Ala Leu Asn Ser Gly Arg Ser Val His Asn Glu
50                  55                  60

Leu Glu Lys Arg Arg Arg Ala Gln Leu Lys Arg Cys Leu Glu Gln Leu
65                  70                  75                  80

Arg Gln Gln Met Pro Leu Gly Val Asp Cys Thr Arg Tyr Thr Thr Leu
                85                  90                  95

Ser Leu Leu Arg Ala Arg Val His Ile Gln Lys Leu Glu Glu Gln Glu
                100                 105                 110

Gln Gln Ala Arg Arg Leu Lys Glu Lys Leu Arg Ser Lys Gln Gln Ser
            115                 120                 125

Leu Gln Gln Gln Leu Glu Gln Leu Gln Gly Leu Pro Gly Ala Arg Glu
130                 135                 140

Arg Glu Arg Leu Arg Ala Asp Ser Leu Asp Ser Ser Gly Leu Ser Ser
145                 150                 155                 160

Glu Arg Ser Asp Ser Asp Gln Glu Asp Leu Glu Val Asp Val Glu Asn
                165                 170                 175

Leu Val Phe Gly Thr Glu Thr Glu Leu Leu Gln Ser Phe Ser Ala Gly
                180                 185                 190

Arg Glu His Ser Tyr Ser His Ser Thr Cys Ala Trp Leu
                195                 200                 205
```

<210> SEQ ID NO 17
<211> LENGTH: 206
<212> TYPE: PRT
<213> ORGANISM: Homo sapiens
<220> FEATURE:
<221> NAME/KEY: UNSURE
<222> LOCATION: (133)...(133)
<223> OTHER INFORMATION: Any amino acid

<400> SEQUENCE: 17

```
Met Glu Pro Leu Ala Ser Asn Ile Gln Val Leu Leu Gln Ala Ala Glu
1               5                   10                  15

Phe Leu Glu Arg Arg Glu Arg Glu Ala Glu His Gly Tyr Ala Ser Leu
```

```
                    20                  25                  30

Cys Pro His Arg Ser Pro Gly Pro Ile His Arg Arg Lys Lys Arg Pro
            35                  40                  45

Pro Gln Ala Pro Gly Ala Gln Asp Ser Gly Arg Ser Val His Asn Glu
        50                  55                  60

Leu Glu Lys Arg Arg Ala Gln Leu Lys Arg Cys Leu Glu Arg Leu
65                  70                  75                  80

Lys Gln Gln Met Pro Leu Gly Gly Asp Cys Ala Arg Tyr Thr Thr Leu
                85                  90                  95

Ser Leu Leu Arg Arg Ala Arg Met His Ile Gln Lys Leu Glu Asp Gln
                100                 105                 110

Glu Gln Arg Ala Arg Gln Leu Lys Glu Arg Leu Arg Thr Lys Gln Gln
            115                 120                 125

Ser Leu Gln Arg Xaa Trp Met Gln Leu Arg Gly Leu Ala Gly Ala Ala
        130                 135                 140

Glu Arg Glu Arg Leu Arg Ala Asp Ser Leu Asp Ser Ser Gly Leu Ser
145                 150                 155                 160

Ser Glu Arg Ser Asp Ser Asp Gln Glu Glu Leu Glu Val Asp Val Glu
                165                 170                 175

Ser Leu Val Phe Gly Gly Glu Ala Glu Leu Leu Arg Gly Phe Val Ala
                180                 185                 190

Gly Gln Glu His Ser Tyr Ser His Val Gly Gly Ala Trp Leu
            195                 200                 205

<210> SEQ ID NO 18
<211> LENGTH: 206
<212> TYPE: PRT
<213> ORGANISM: Homo sapiens
<220> FEATURE:
<221> NAME/KEY: UNSURE
<222> LOCATION: (133)...(133)
<223> OTHER INFORMATION: Any amino acid

<400> SEQUENCE: 18

Met Glu Pro Leu Ala Ser Asn Ile Gln Val Leu Leu Gln Ala Ala Glu
 1               5                  10                  15

Phe Leu Glu Arg Arg Glu Arg Glu Ala Glu His Gly Tyr Ala Ser Leu
                20                  25                  30

Cys Pro His Arg Ser Pro Gly Pro Ile His Arg Arg Lys Lys Arg Pro
            35                  40                  45

Pro Gln Ala Pro Gly Ala Gln Asp Ser Gly Arg Ser Val His Asn Glu
        50                  55                  60

Leu Glu Lys Arg Arg Ala Gln Leu Lys Arg Cys Leu Glu Arg Leu
65                  70                  75                  80

Lys Gln Gln Met Pro Leu Gly Gly Asp Cys Ala Arg Tyr Thr Thr Leu
                85                  90                  95

Ser Leu Leu Arg Arg Ala Arg Met His Ile Gln Lys Leu Glu Asp Gln
                100                 105                 110

Glu Gln Arg Ala Arg Gln Leu Lys Glu Arg Leu Arg Thr Lys Gln Gln
            115                 120                 125

Ser Leu Gln Arg Xaa Trp Met Gln Leu Arg Gly Leu Ala Gly Ala Ala
        130                 135                 140

Glu Arg Glu Arg Leu Arg Ala Asp Ser Leu Asp Ser Ser Gly Leu Ser
145                 150                 155                 160

Ser Glu Arg Ser Asp Ser Asp Gln Glu Glu Leu Glu Val Asp Val Glu
                165                 170                 175
```

```
Ser Leu Val Phe Gly Gly Glu Ala Glu Leu Leu Arg Gly Phe Val Ala
            180                 185                 190

Gly Gln Glu His Ser Tyr Ser His Val Gly Gly Ala Trp Leu
        195                 200                 205
```